(12) United States Patent
Kukita et al.

(10) Patent No.: US 9,226,668 B2
(45) Date of Patent: Jan. 5, 2016

(54) BLOOD PRESSURE MONITOR

(75) Inventors: Tomohiro Kukita, Kyoto (JP); Yukiko Mitsunami, Otsu (JP); Kenji Aritome, Ibaraki (JP); Hiroyuki Kato, Kyoto (JP); Yoshihide Onishi, Liaoning (CN)

(73) Assignee: OMRON HEALTHCARE Co., Ltd., Kyoto (JP)

( * ) Notice: Subject to any disclaimer, the term of this patent is extended or adjusted under 35 U.S.C. 154(b) by 415 days.

(21) Appl. No.: 12/741,320

(22) PCT Filed: Nov. 5, 2008

(86) PCT No.: PCT/JP2008/070102
§ 371 (c)(1),
(2), (4) Date: May 4, 2010

(87) PCT Pub. No.: WO2009/060850
PCT Pub. Date: May 14, 2009

(65) Prior Publication Data
US 2010/0249615 A1 Sep. 30, 2010

(30) Foreign Application Priority Data
Nov. 6, 2007 (JP) ................................. 2007-288743

(51) Int. Cl.
*A61B 5/02* (2006.01)
*A61B 5/022* (2006.01)

(52) U.S. Cl.
CPC ..... *A61B 5/02233* (2013.01); *A61B 2560/0261* (2013.01)

(58) Field of Classification Search
CPC .................... A61B 5/02233; A61B 2560/0261
USPC .................................................. 600/490–499
See application file for complete search history.

(56) References Cited

U.S. PATENT DOCUMENTS 4,747,412 A * 5/1988 Yamaguchi .................... 600/496
6,932,772 B2 * 8/2005 Kan .............................. 600/490
(Continued)

FOREIGN PATENT DOCUMENTS

EP 0 778 001 B1 4/2004
EP 1 568 313 A1 8/2005
(Continued)

OTHER PUBLICATIONS

Patent Abstracts of Japan, Publication No. 2005-237802, dated Sep. 8, 2005, 1 page.
(Continued)

*Primary Examiner* — Patricia Mallari
*Assistant Examiner* — Tiffany Weston
(74) *Attorney, Agent, or Firm* — Osha Liang LLP

(57) ABSTRACT

A blood pressure monitor includes a cuff to be wound around a living body of a subject, a measuring unit for measuring blood pressure with said cuff wound around the living body of said subject, a detecting unit for detecting an inclination angle of said cuff, a specifying unit for specifying a current inclination level among a plurality of predetermined inclination levels upon measurement by said measuring unit, based on a result of detection by said detecting unit, a memory for storing therein the inclination level specified by said specifying unit, in association with blood pressure data measured by said measuring unit, and a notifying unit for providing notification of at least one past inclination level of the plurality of inclination levels stored in said memory and said current inclination level, in association with each other.

7 Claims, 23 Drawing Sheets

(56) References Cited

U.S. PATENT DOCUMENTS

| | | | |
|---|---|---|---|
| 7,214,193 B2* | 5/2007 | Freund et al. | 600/490 |
| 2005/0187484 A1* | 8/2005 | Sano et al. | 600/495 |
| 2005/0192501 A1* | 9/2005 | Sano et al. | 600/499 |

FOREIGN PATENT DOCUMENTS

| | | |
|---|---|---|
| JP | 3-231630 A | 10/1991 |
| JP | 2001-112724 A | 4/2001 |
| JP | 2003-093355 A | 4/2003 |
| JP | 2004-223108 A | 8/2004 |
| JP | 2005-237802 A | 9/2005 |
| JP | 2006-122144 A | 5/2006 |
| RU | 2 140 187 C1 | 10/1999 |
| RU | 2 177 245 C2 | 12/2001 |

OTHER PUBLICATIONS

Patent Abstracts of Japan, Publication No. 2003-093355, dated Apr. 2, 2003, 1 page.

Patent Abstracts of Japan, Publication No. 2001-112724, dated Apr. 24, 2001, 1 page.

International Search Report issued in PCT/JP2008/070102, mailed on Dec. 2, 2008, with translation, 2 pages.

Office Action for Russian Application No. 2010122986 mailed Nov. 5, 2008, with English translation thereof (13 pages).

Patent Abstract for Russian Publication No. 2 177 245 Published Dec. 27, 2001 (1 page).

Patent Abstract for Russian Publication No. 2 140 187 Published Oct. 27, 1999 (1 page).

C.J. de Ruiter, et al., "Knee Angle-Dependent Oxygen Consumption During Isometric Contractions of the Knee Extensors Determined with Near-Infrared Spectroscopy", Cheshire, UK, Published online before print Mar. 2005 (9 pages).

T. Ueno, "Cranial Diameter Pulsations Measured by Non-Invasive Ultrasound Decrease with Tilt", Alexandria, VA, Aug. 2003 (1 page).

Patent Abstracts of Japan, Publication No. JP2006-122144, dated May 18, 2006, 1 page.

Patent Abstracts of Japan, Publication No. JP2004-223108, dated Aug. 12, 2004, 1 page.

Patent Abstracts of Japan, Publication No. JP3-231630, dated Oct. 15, 1991, 1 page.

Decision to Grant a Patent issued in corresponding Japanese Application No. 2007-288743, mailed Dec. 27, 2011, with translation, 6 pages.

* cited by examiner

FIG.18
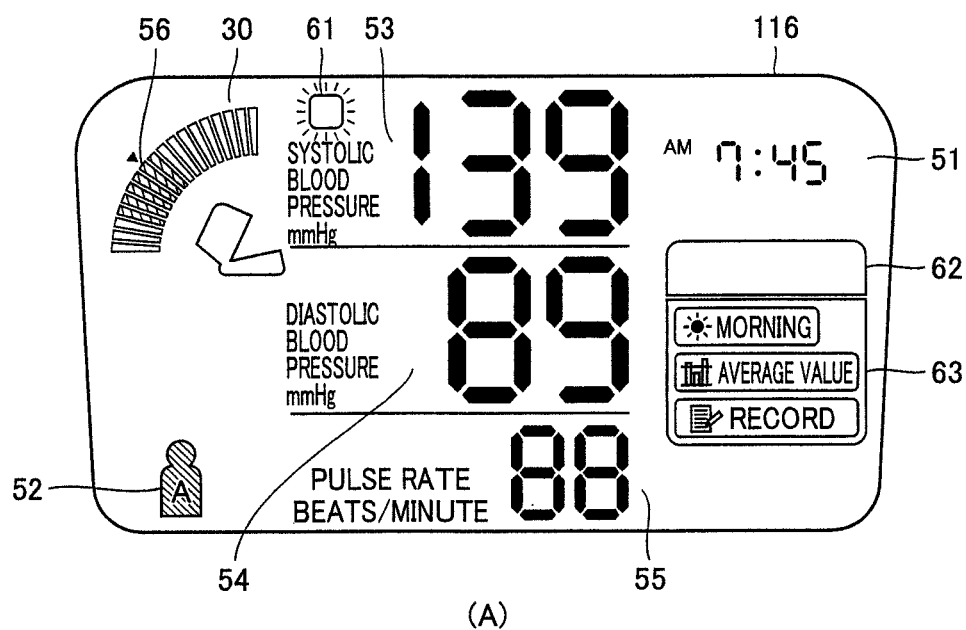
(A)
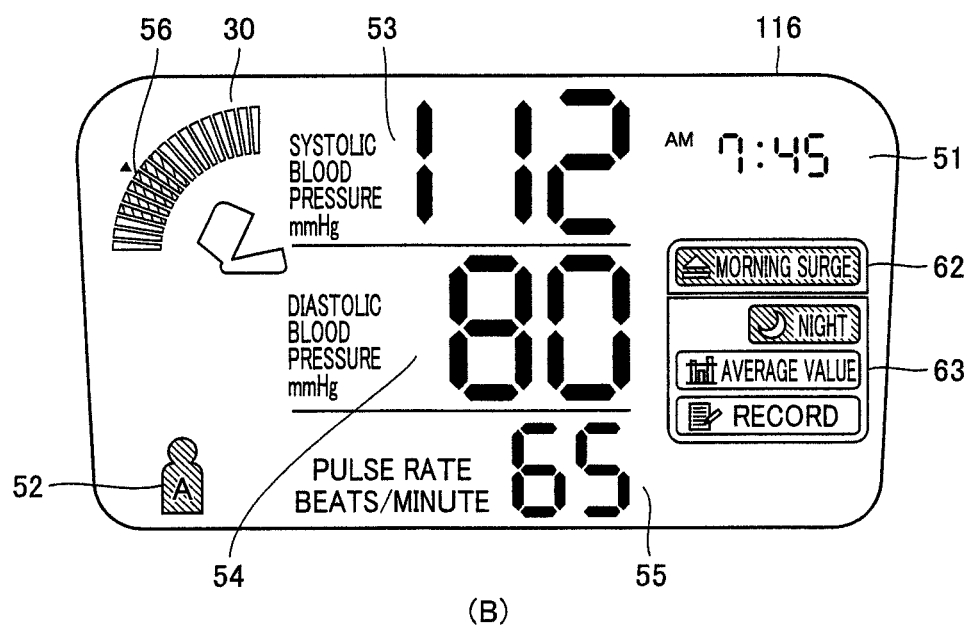
(B)

BLOOD PRESSURE MONITOR

TECHNICAL FIELD

The present invention relates to a blood pressure monitor, in particular, a (for example, household) blood pressure monitor capable of recording a blood pressure value.

BACKGROUND ART

In recent years, as daily health management, importance has been placed on daily measurement and management of blood pressure values. Accordingly, household blood pressure monitors have been pervasive. Each of such blood pressure monitors records blood pressure values on daily basis, displays changes of blood pressure values with passage of time, and is therefore used for diagnosis for cardiovascular risks.

In order to ascertain the daily changes of blood pressure values, it is necessary to eliminate fluctuation factors having influence over the blood pressure values in such a blood pressure monitor.

For example, Japanese Patent Laying-Open No. 2003-93355 (patent document 1) and Japanese Patent Laying-Open No. 2001-112724 (patent document 2) disclose that TPO (Time, Place, Occasion) information for measurement or information about a measurement condition (such as alcohol drinking) is added to measurement information such as a measured blood pressure value. In this way, an influence of the TPO information for the measurement or the condition of measurement over the measurement value, as well as tendency thereof can be figured out.

Meanwhile, a subject's posture for measurement is important for accurate measurement of blood pressure. For example, Japanese Patent Laying-Open No. 2005-237802 (patent document 3) proposes a blood pressure monitor provided with an automatic cuff winding mechanism for automatically winding a cuff around an upper arm of a subject, so as to lead the subject into a natural posture during measurement without making the subject feel uncomfortable. In such a blood pressure monitor, constant winding strength is reproduced for each measurement, which ensures stable and accurate measurement and also eliminates the burdensome, cuff winding job, advantageously.

The invention of patent document 3 includes: a first enclosure rested on a table; a second enclosure, having an approximately cylindrical shape, located on the first enclosure in a non-use state, and having a cuff arranged on its inner peripheral surface, the cuff having a hollow opening to which a portion of a living body of a subject is inserted; and a connection mechanism for connecting the second enclosure with the first enclosure in a movable manner such that, upon application of the cuff to the subject, the second enclosure can move to come closer to the subject relative to the first enclosure. In this way, the blood pressure of the subject can be measured with the back straight, thus achieving accurate and stable measurement of blood pressure. Patent document 3 also discloses that upon the measurement, it is determined whether or not the inclination level of the second enclosure is within a predetermined optimal measurement range, and the subject is notified of a result of the determination. In this way, the subject can know whether or not the current inclination level falls within the optimal measurement range.

Patent document 1: Japanese Patent Laying-Open No. 2003-93355

Patent document 2: Japanese Patent Laying-Open No. 2001-112724

Patent document 3: Japanese Patent Laying-Open No. 2005-237802

DISCLOSURE OF THE INVENTION

Problems to be Solved by the Invention

Japanese Patent Laying-Open No. 2003-93355 (patent document 1) and Japanese Patent Laying-Open No. 2001-112724 (patent document 2) do not disclose that information about a posture for measurement is recorded. Accordingly, it cannot be figured out how a difference in posture for measurement affects blood pressure values.

Meanwhile, in Japanese Patent Laying-Open No. 2005-237802 (patent document 3), although the subject can adjust the posture for measurement to bring the current inclination level of the second enclosure into the optimal measurement range (recommended inclination range), it is difficult to lead the subject into the same position every time.

The present invention is made to solve the above-described problem, and its object is to provide a blood pressure monitor capable of adjusting a subject's posture for measurement so that the subject takes the same posture as that in past.

Means for Solving the Problems

A blood pressure monitor according to a certain aspect of the present invention includes: a cuff to be wound around a living body of a subject; a measuring unit for measuring blood pressure with the cuff wound around the living body of the subject; a detecting unit for detecting an inclination angle of the cuff; a specifying unit for specifying a current inclination level among a plurality of predetermined inclination levels upon measurement by the measuring unit, based on a result of detection by the detecting unit; a memory for storing therein the inclination level specified by the specifying unit, in association with blood pressure data measured by the measuring unit; and a notifying unit for providing notification of at least one past inclination level of the plurality of inclination levels stored in the memory and the current inclination level, in association with each other.

Preferably, the blood pressure monitor further includes: a first enclosure to be placed on a placement table; a second enclosure having an approximately cylindrical shape, located on the first enclosure in a non-use state, and having an inner peripheral surface on which the cuff is disposed; and a connecting portion for connecting the second enclosure to the first enclosure in a freely movable manner such that upon applying the cuff to the subject with the first enclosure being placed on the placement table, the second enclosure is movable toward the subject from a location where the second enclosure is in the non-use state, wherein the detecting unit detects an inclination angle of the second enclosure.

Preferably, the blood pressure monitor further includes a search unit for searching for and reading out a most recent inclination level of the plurality of inclination levels stored in the memory, wherein the notifying unit provides notification of the most recent inclination level thus read out by the search unit, as the past inclination level.

Alternatively, the blood pressure monitor preferably further includes a statistics calculating unit for calculating a statistical value of the plurality of inclination levels stored in the memory, wherein the notifying unit provides notification of the past inclination level, based on a result of calculation by the statistics calculating unit.

Preferably, the statistics calculating unit includes a frequency calculating unit for calculating respective frequencies of the plurality of inclination levels, and as a result of calculation by the frequency calculating unit, the notifying unit provides notification of a most frequent inclination level as the past inclination level.

Alternatively, the blood pressure monitor preferably further includes a search unit for searching for and reading out a most recent inclination level falling within a predetermined range, among the plurality of inclination levels stored in the memory, wherein the notifying unit provides notification of the inclination level thus searched by the search unit, as the past inclination level.

Alternatively, the blood pressure monitor preferably further includes: an extracting unit for extracting inclination levels falling within a predetermined range, among the plurality of inclination levels stored in the memory; and a statistics calculating unit for calculating a statistical value of the inclination levels extracted by the extracting unit, wherein the notifying unit provides notification of the past inclination level based on a result of calculation by the statistics calculating unit.

Preferably, the statistics calculating unit includes a frequency calculating unit for calculating respective frequencies of the inclination levels extracted, and as a result of calculation by the frequency calculating unit, the notifying unit provides notification of a most frequent inclination level as the past inclination level.

Preferably, the blood pressure monitor further includes a determining unit for determining whether or not the current inclination level specified falls within a predetermined range, wherein when the determining unit determines that the current inclination level falls within the predetermined range, the memory stores the current level therein.

Preferably, the notifying unit includes a display control unit for performing control for displaying the past inclination level and the current inclination level in association with each other, and a display for displaying based on an output from the display control unit.

Preferably, the display control unit performs control for displaying in a graph the plurality of inclination levels stored in the memory.

More preferably, the first enclosure includes a contact surface in contact with the placement table, the detecting unit also detects a degree of levelness of the contact surface, and the notifying unit also provides notification of the degree of levelness.

More preferably, the blood pressure monitor further includes a distance detecting unit for detecting a distance to a trunk of the subject, wherein the notifying unit also provides notification that the distance detected by the distance detecting unit falls out of a predetermined distance.

Effects of the Invention

According to the present invention, a subject can adjust a posture for measurement so that a current inclination level matches with a past inclination level. In this way, daily changes in blood pressure value can be accurately figured out.

Each of FIGS. 18(A), (B) shows an exemplary screen displaying measurement record data to provide a record of measurement in each embodiment of the present invention.

Figure 19:
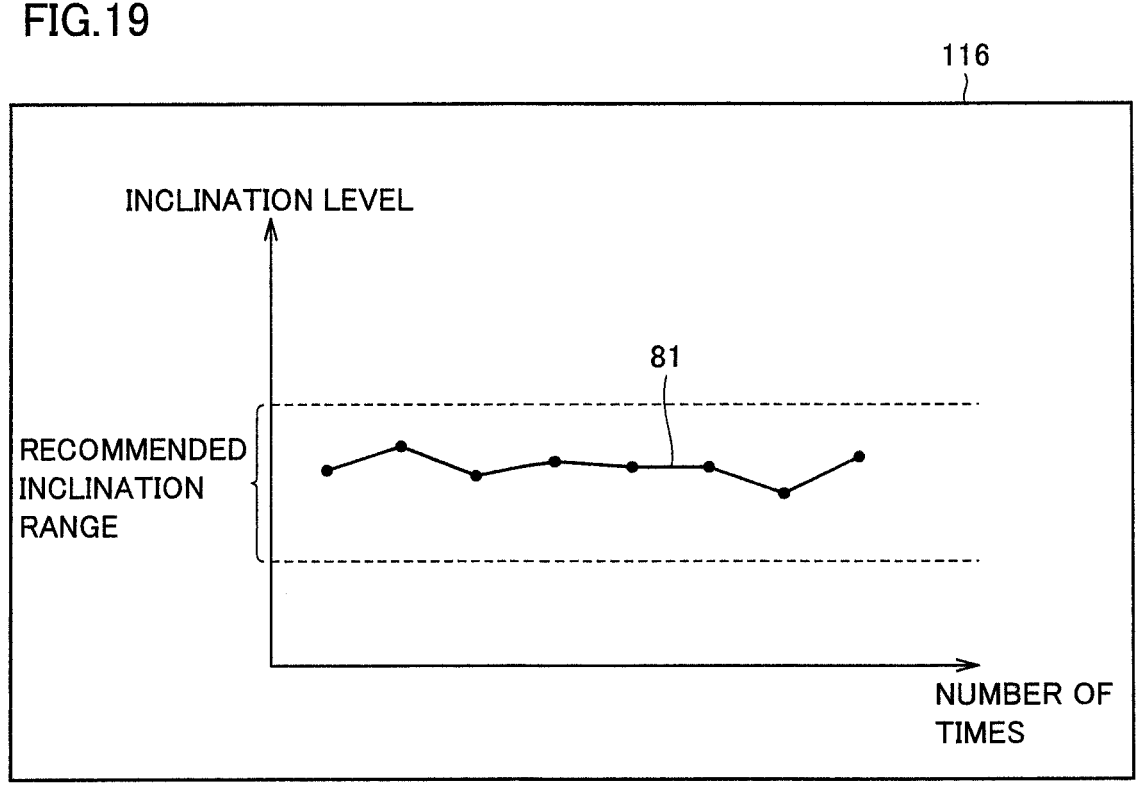

FIG. 19 shows one exemplary screen displaying a graph indicating changes in inclination level.

Figure 20:
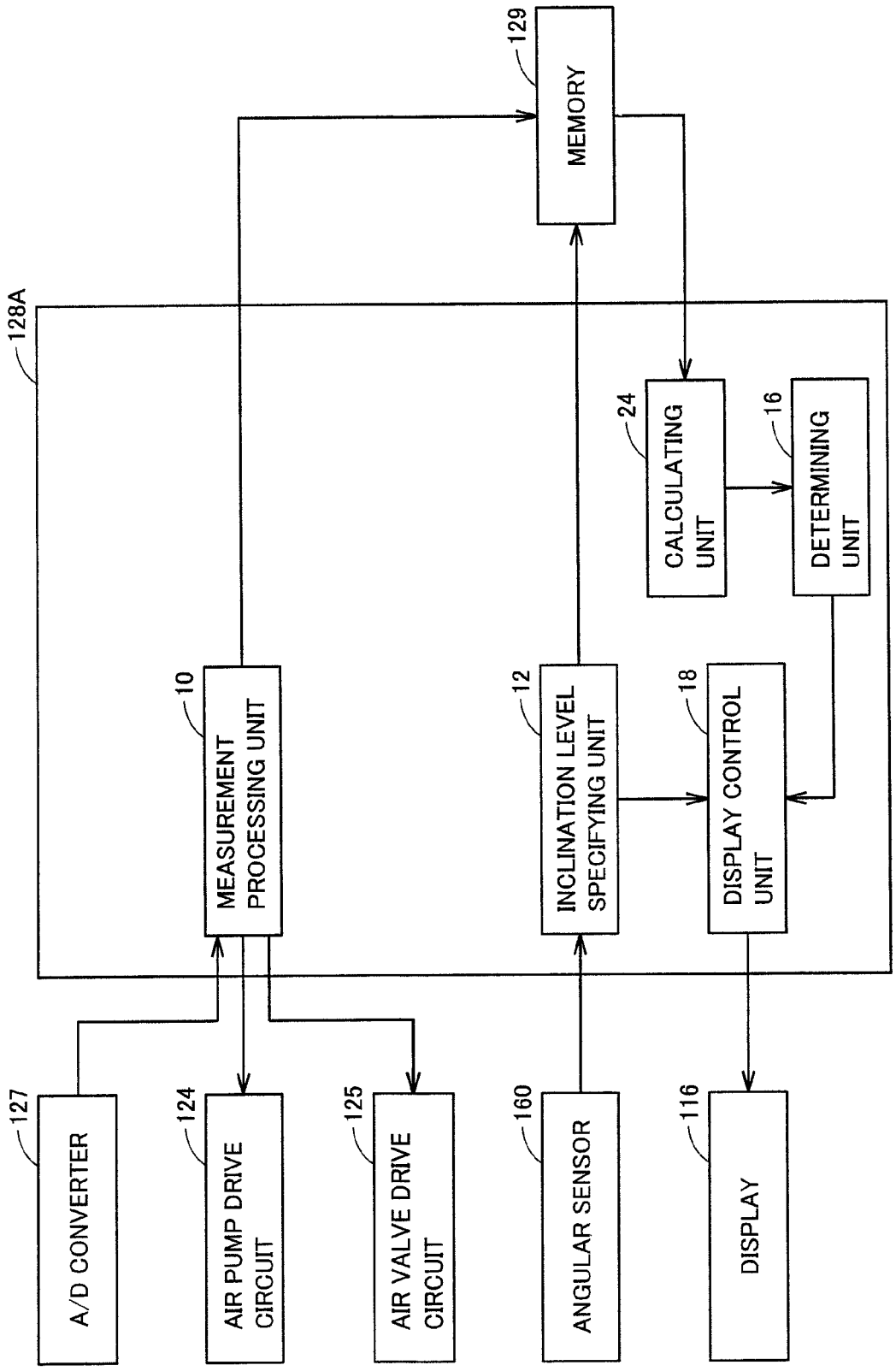

FIG. 20 is a functional block diagram of a blood pressure monitor of a first variation of the first embodiment of the present invention.

Figure 21:
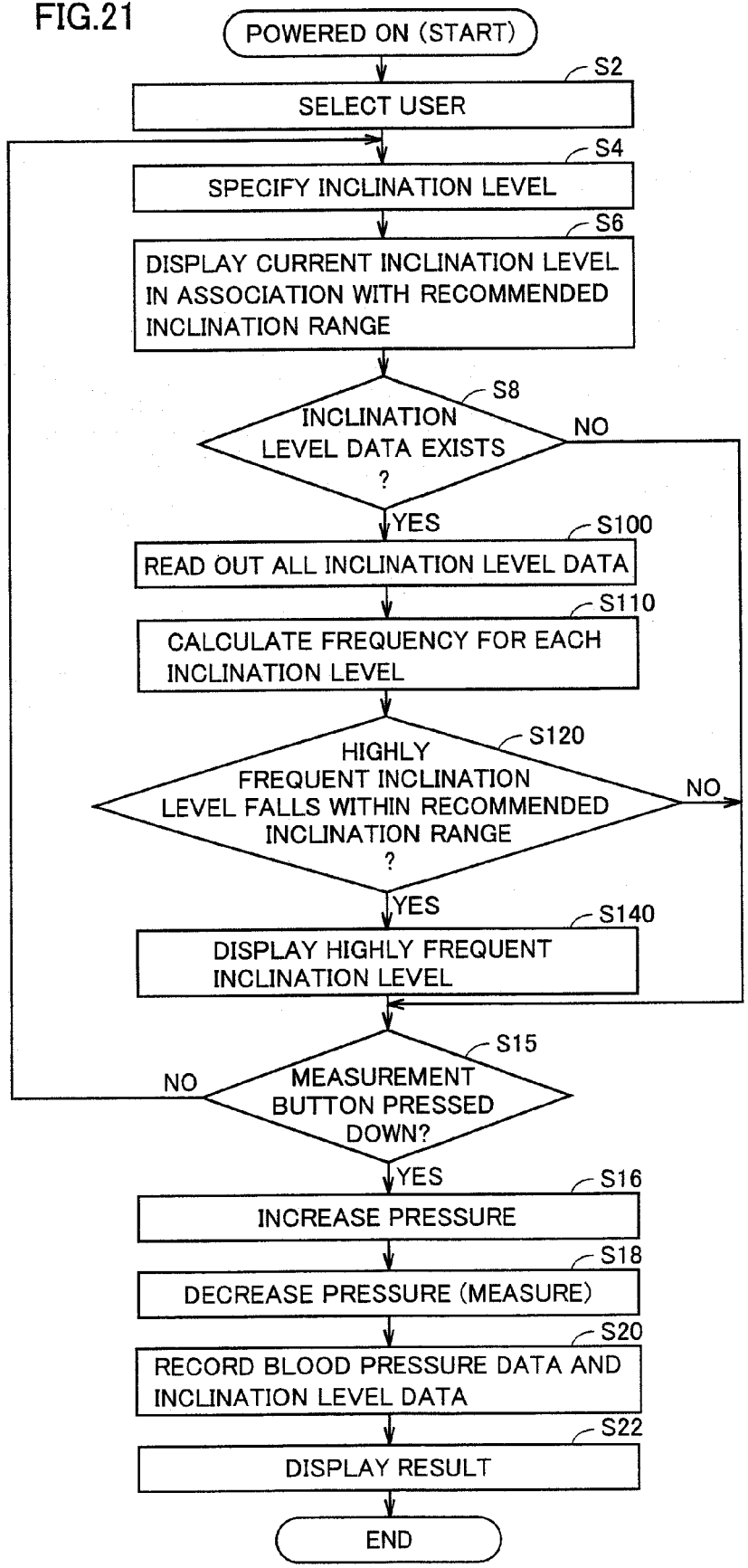

FIG. 21 is a flowchart showing blood pressure measuring/recording processing performed in the blood pressure monitor of the first variation of the first embodiment of the present invention.

Figure 22:
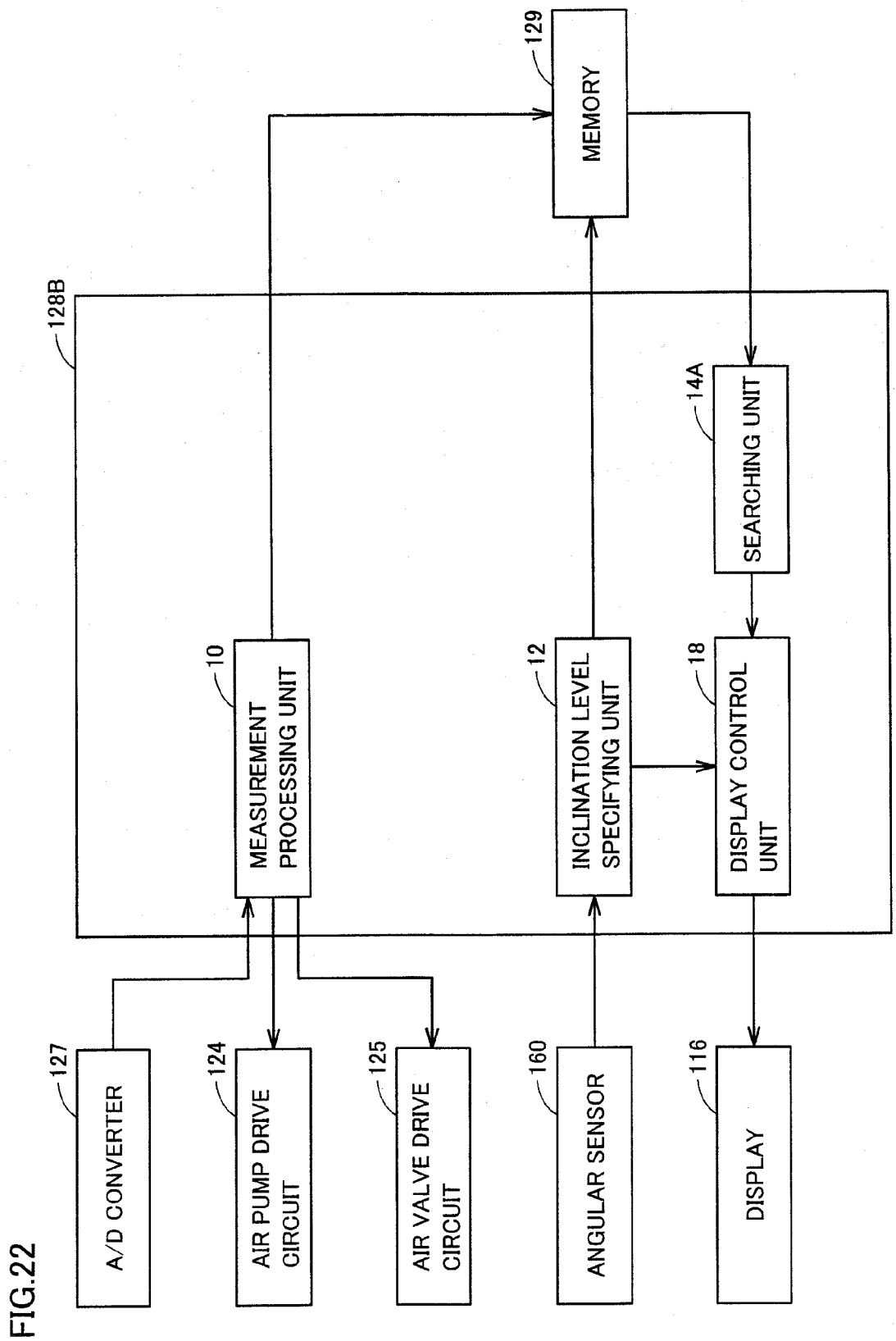

FIG. 22 is a functional block diagram of a blood pressure monitor of a second variation of the first embodiment of the present invention.

Figure 23:
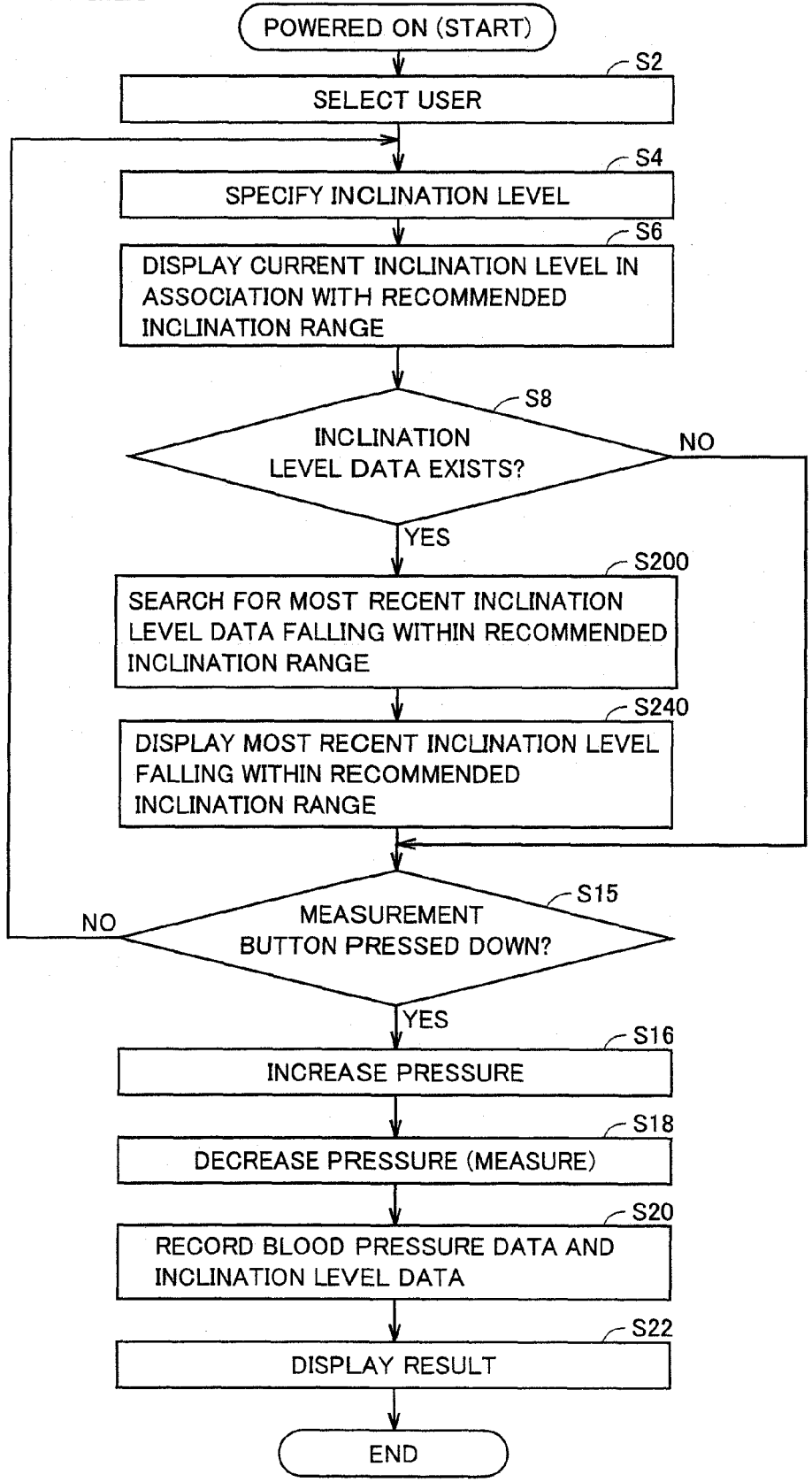

FIG. 23 is a flowchart showing blood pressure measuring/recording processing performed in the blood pressure monitor of the second variation of the first embodiment of the present invention.

Figure 24:
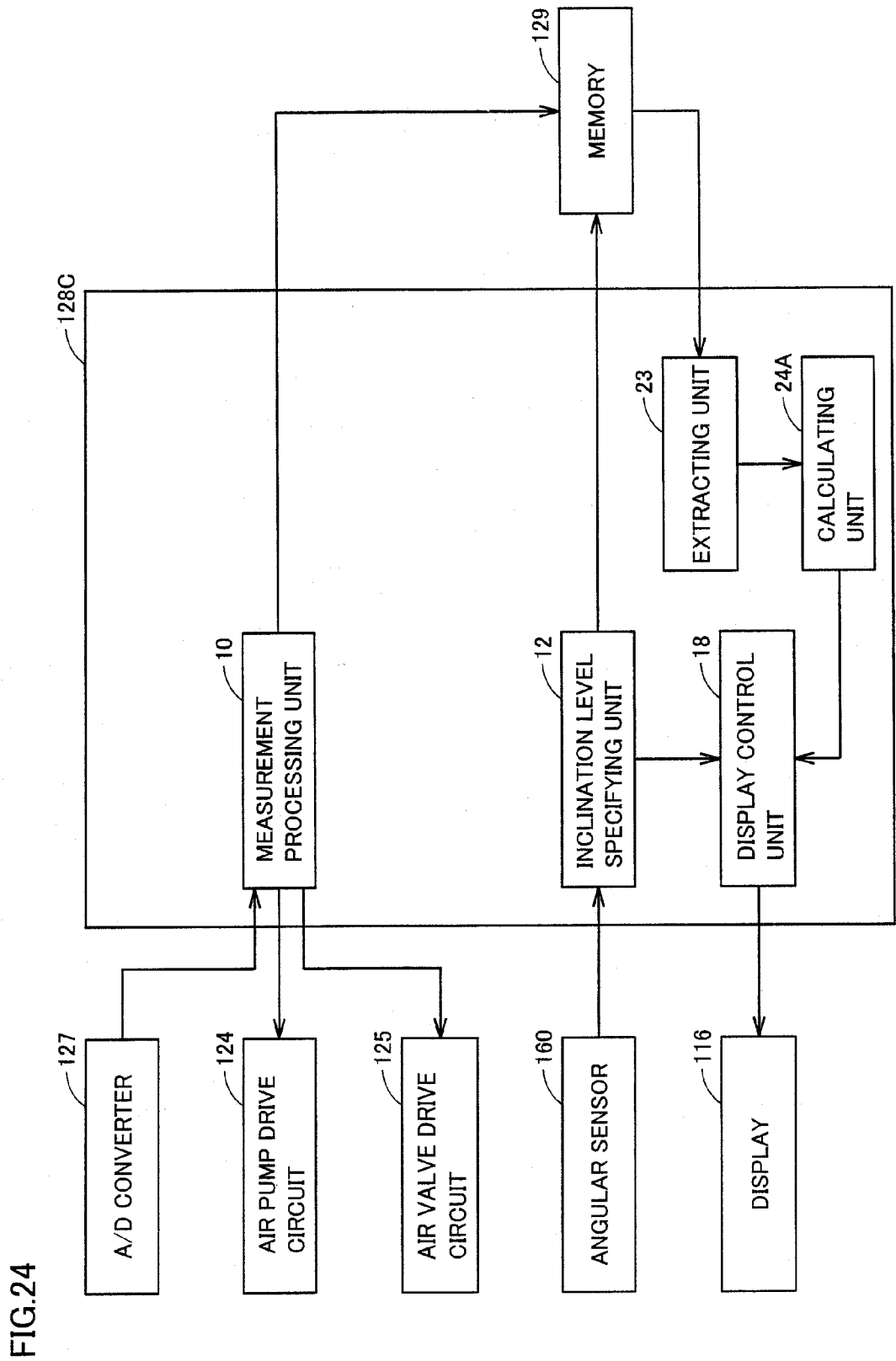

FIG. 24 is a functional block diagram of a blood pressure monitor of a third variation of the first embodiment of the present invention.

Figure 25:
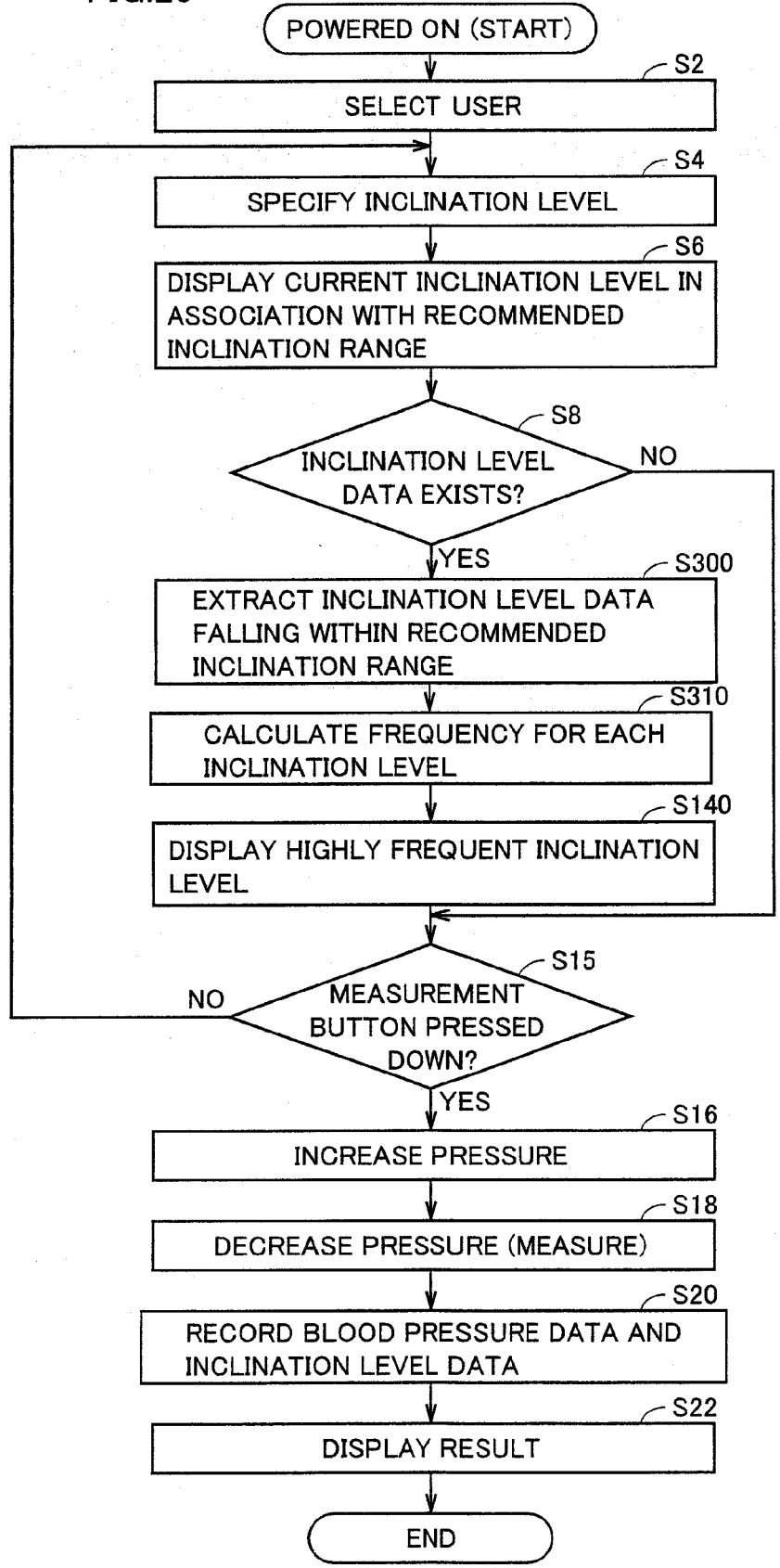

FIG. 25 is a flowchart showing blood pressure measuring/recording processing performed in the blood pressure monitor of the third variation of the first embodiment of the present invention.

Figure 26:
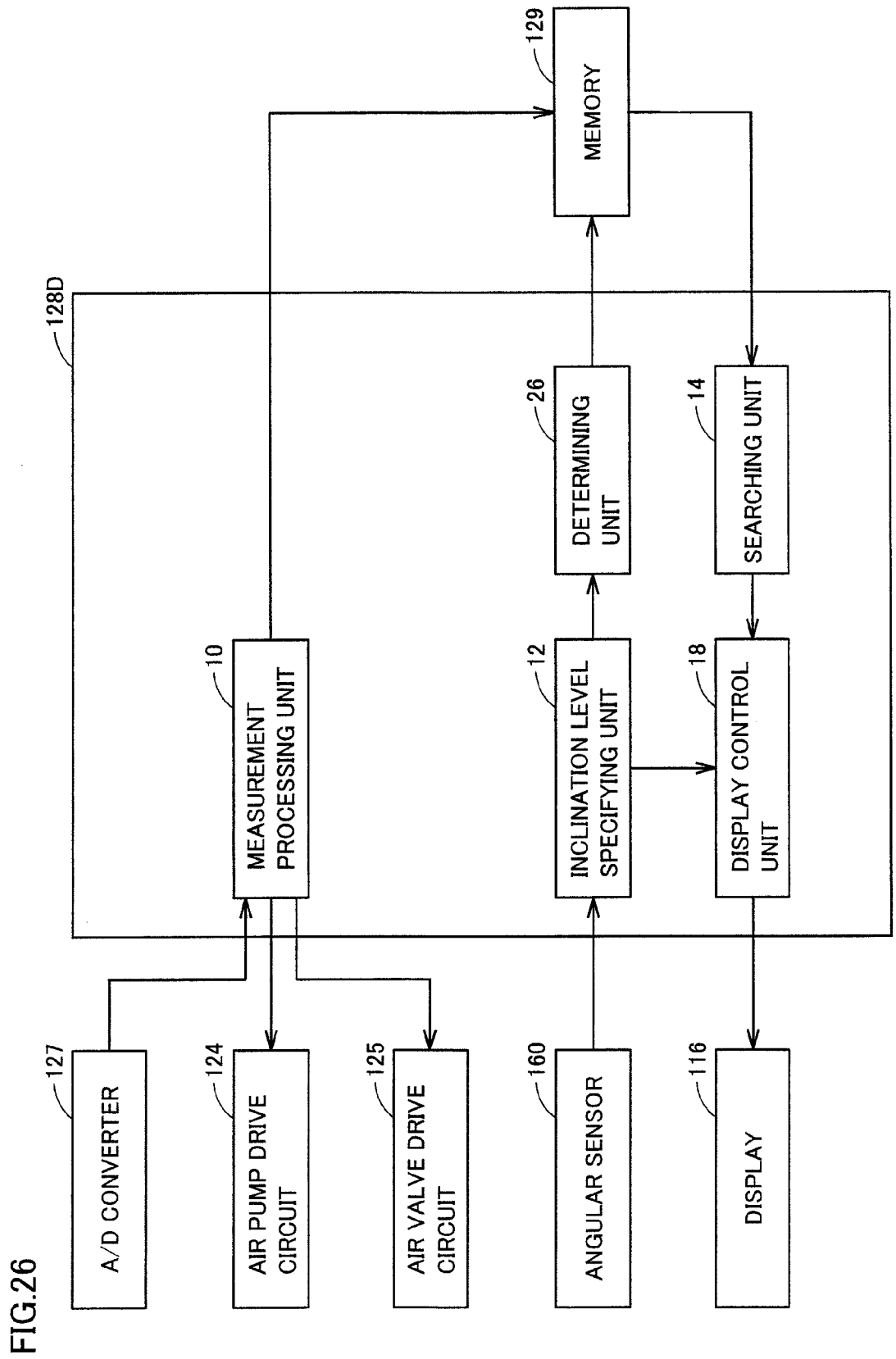

FIG. 26 is a functional block diagram of a blood pressure monitor of a second embodiment of the present invention.

Figure 27:
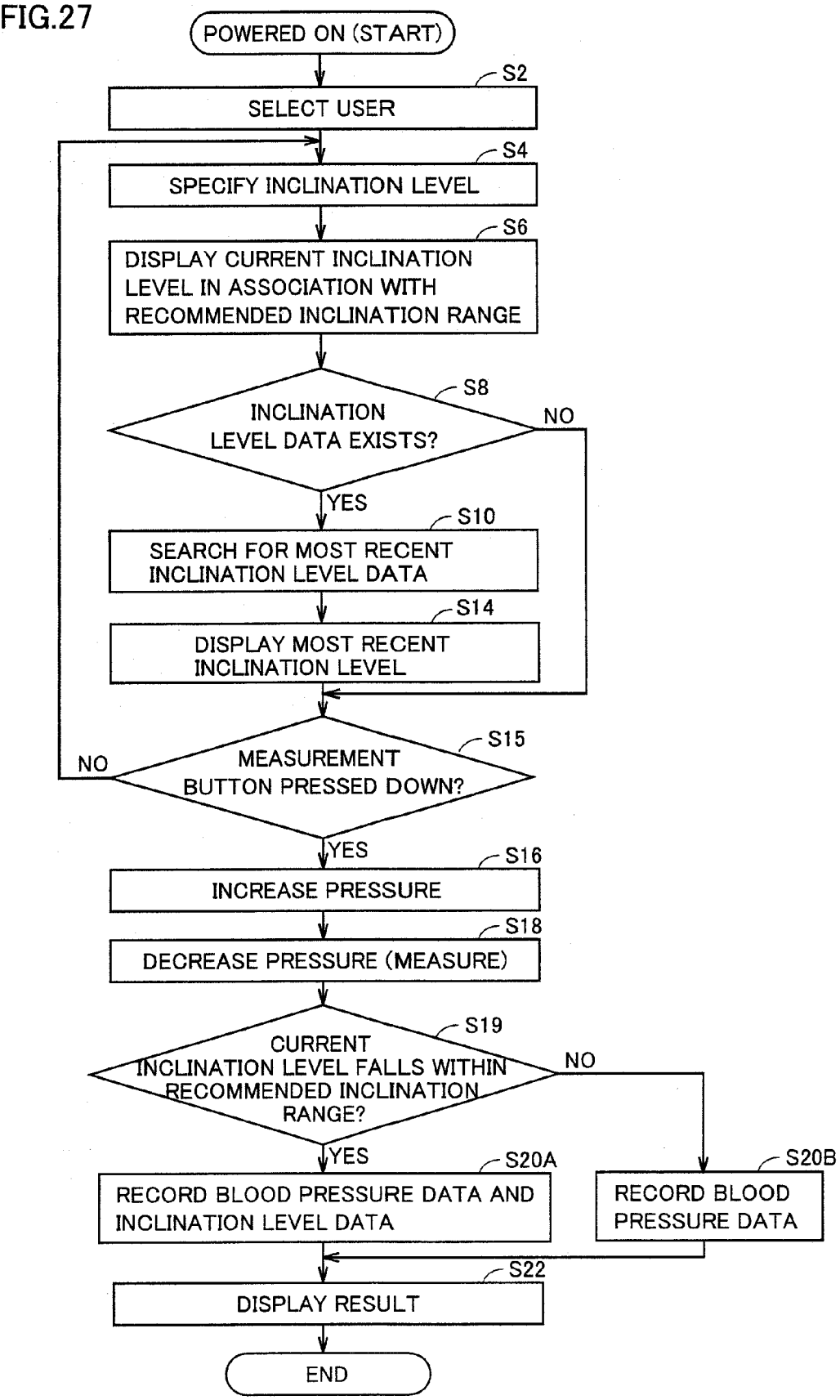

FIG. 27 is a flowchart showing blood pressure measuring/recording processing performed in the blood pressure monitor of the second embodiment of the present invention.

DESCRIPTION OF THE REFERENCE SIGNS

10: measurement processing unit; 12: inclination level specifying unit; 14, 14A: search unit; 16, 26: determining unit; 18: display control unit; 23: extracting unit; 24, 24A: calculating unit; 30: block set; 35: pictogram; 100: blood pressure monitor; 110: main unit; 112: main unit casing; 114: control portion; 116: display portion; 118: laser output unit; 120: living body pressing air system; 121: air pump; 122: air valve; 123: pressure sensor; 124: air pump drive circuit; 125: air valve drive circuit; 126: amplifier; 127: A/D converter; 128, 128A, 128B, 128C, 128D: CPU; 129: memory; 129A, 129B: measurement result storage area; 130: timer; 140: living body insert portion; 141: hinge portion; 142: living body insert portion casing; 144: handle; 145: cuff; 146: unlocking button; 148: cuff cover; 150: hollow opening; 152: living body pressing air bag; 154: air tube; 160: angular sensor; 210: desk; 220: chair; 300: subject; 310: forearm; 320: upper atm; 330: heart; 420: horizontal plane; AGi: inclination level data; DBPi: diastolic blood pressure data; DTi: measurement date/time data; PLSi: pulse rate data; SBPi: systolic blood pressure data.

BEST MODES FOR CARRYING OUT THE INVENTION

Embodiments of the present invention will be described in detail with reference to figures. It should be noted that the same or equivalent portions in the figures are given the same reference characters and are not described repeatedly.

First Embodiment

As to External Structure and Posture for Measurement

Figure 1:
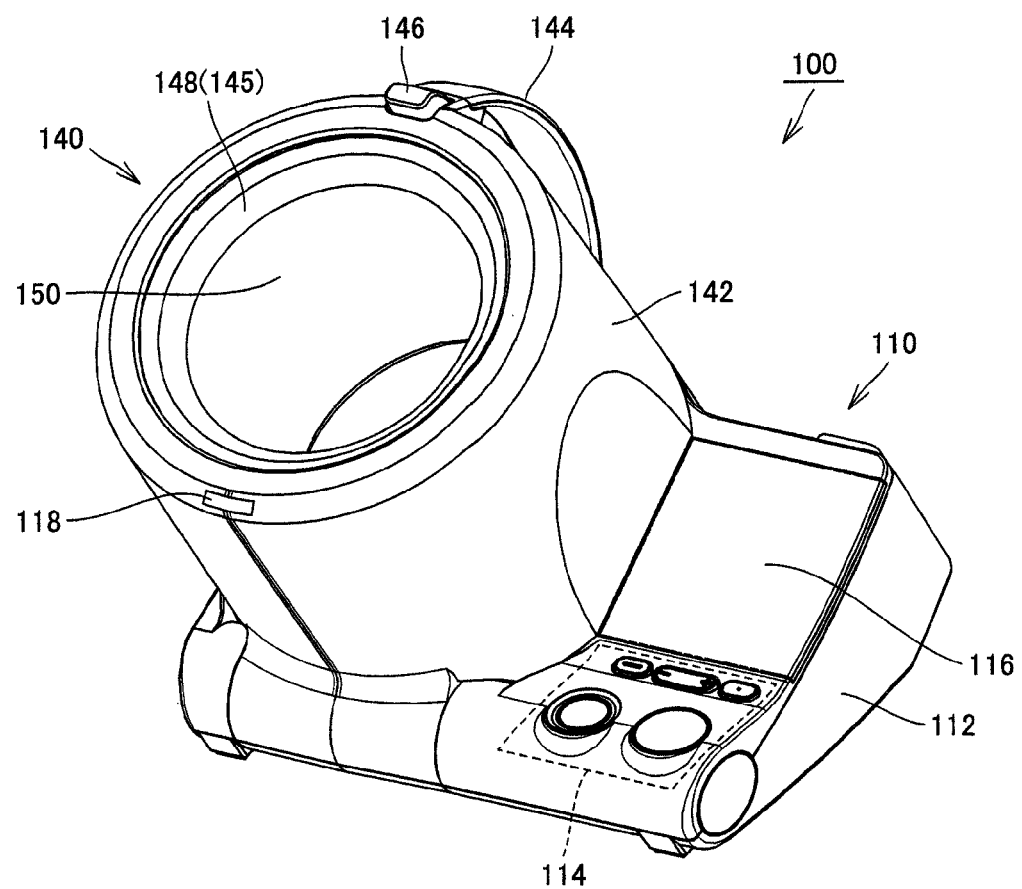
FIG. 1 is a perspective view of an external structure of a blood pressure monitor of each embodiment of the present invention when viewed obliquely from the upper right.

FIG. 1 is a perspective view showing an external structure of a blood pressure monitor of a first embodiment of the present invention when viewed obliquely from the upper right.

As shown in FIG. 1, blood pressure monitor 100 according to the present embodiment primarily includes a main unit 110 placed on a placement table such as a desk, and a living body insert portion 140 having a hollow opening 150 to which a subject's upper arm is inserted. Main unit 110 is covered with a main unit casing 112 that is a first enclosure, and living body insert portion 140 is covered with a living body insert portion casing 142 that is a second enclosure.

Provided on the upper surface of main unit 110 is a control portion 114 for receiving an instruction from a subject. Control portion 114 has various buttons, which include a power supply button for turning the power on, a measurement button for starting a measurement operation, a display portion control button for controlling a display portion, and others. A display portion 116 is provided on another part of the upper surface of main unit 110 to display a result of the measurement, operating guides and others. An elbow rest 119 for resting the elbow when the subject takes a posture for measurement is provided at a prescribed position on the upper surface of main unit 110, adjacent to control portion 114 and display portion 116 (see FIG. 2). This elbow rest 119 is, for example, a depression provided on the upper surface of main unit casing 112.

Living body insert portion 140 is connected to main unit 110 in a pivotable manner by means of a pivot connection mechanism including a pivot. Specifically, the pivot, which is arranged within main unit casing 112 at the front end of main unit 110 facing the subject, connects main unit casing 112 with living body insert portion casing 142 in a pivotable manner.

Living body insert portion 140 includes a cuff 145 arranged on the inner peripheral surface of living body insert portion casing 142 of an approximately cylindrical shape, and a cuff cover 148 attached to living body insert portion casing 142 to cover cuff 145. A handle 144 is provided at a prescribed position on the outer peripheral surface of living body insert portion casing 142, and is used by a subject to pivotally move living body insert portion 140. Further, an unlocking button 146 is provided in the vicinity of handle 144, and is used to allow pivotal movement of living body insert portion casing 142 rested on main unit 110.

Figure 2:
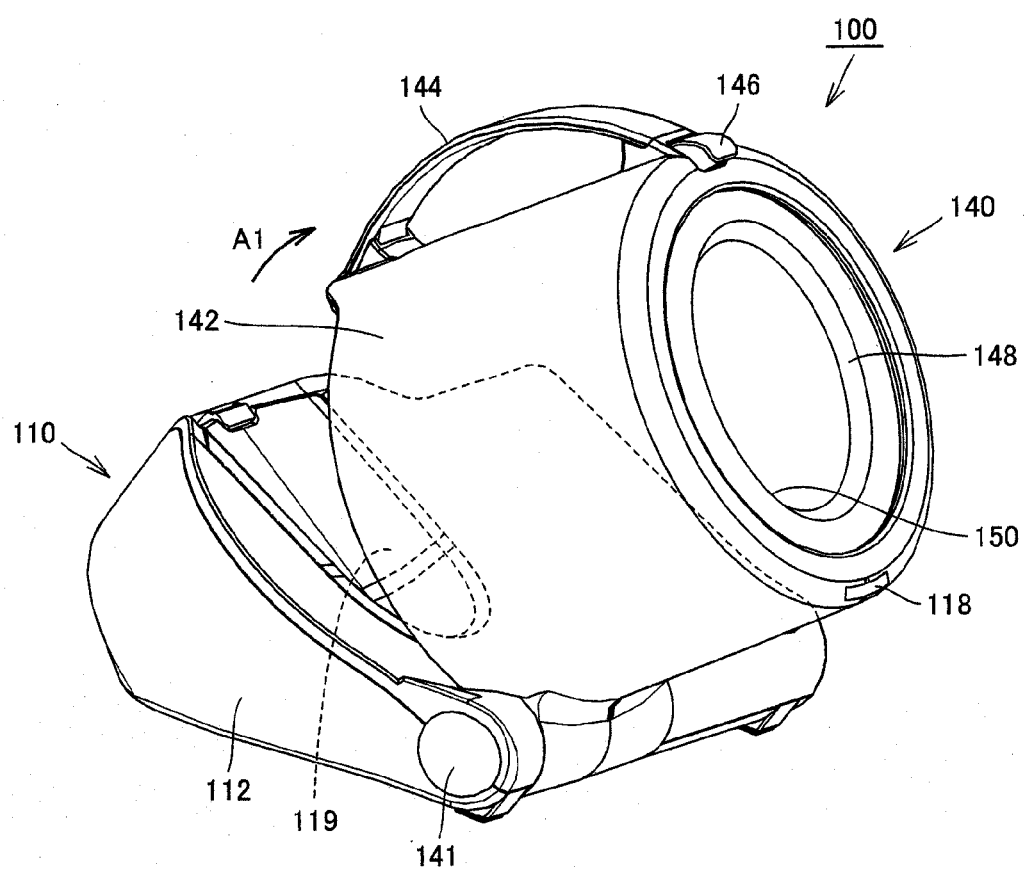
FIG. 2 is a perspective view showing a state in which a living body insert portion of the blood pressure monitor of each embodiment of the present invention is unlocked.

FIG. 2 is a perspective view showing a state in which living body insert portion 140 is unlocked.

Living body insert portion casing 142 is pivoted to move toward the subject (in a direction of an arrow A1 in the figure) around a hinge portion 141, which serves as the pivot connection mechanism including the pivot. In this way, living body insert portion casing 142 thus moved is positioned closer to the subject relative to main unit casing 112.

In the present embodiment, living body insert portion casing 142 has an upper portion (in the vicinity of unlocking button 146) in which a detecting unit, such as an angular sensor 160, is provided to detect an inclination angle of living body insert portion casing 142.

Figure 3:
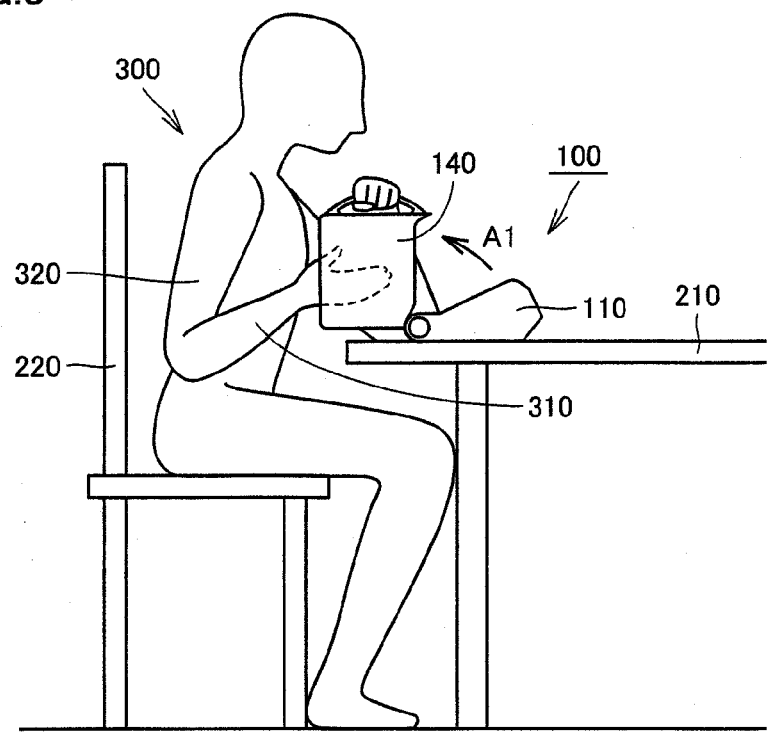
FIG. 3 is a schematic diagram showing a procedure of applying a cuff of the blood pressure monitor of each embodiment of the present invention.
Figure 4:
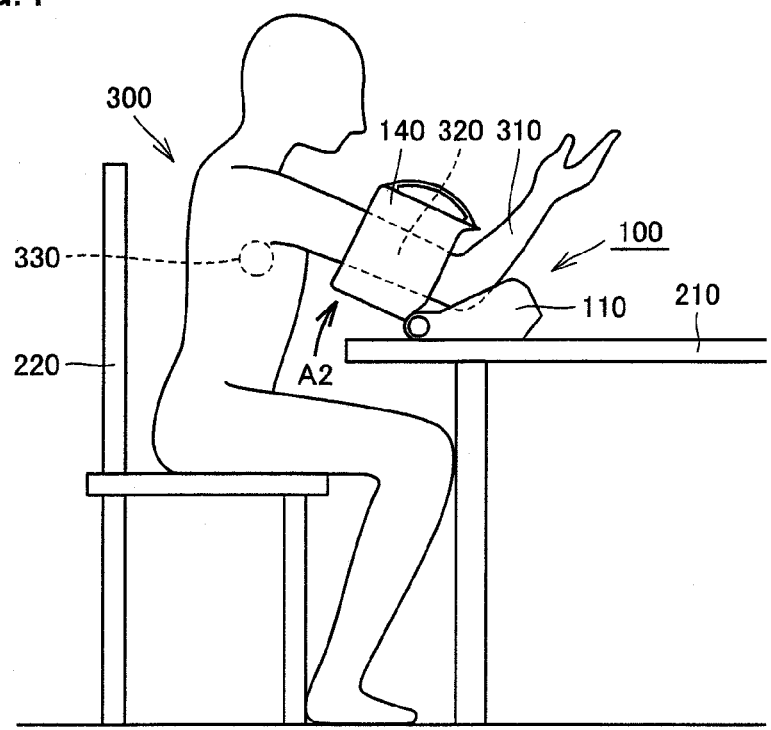
FIG. 4 is a schematic diagram showing a posture for measurement after applying the cuff of the blood pressure monitor of each embodiment of the present invention.

FIG. 3 is a schematic diagram showing a procedure of applying cuff 145 of blood pressure monitor 100 of the first embodiment of the present invention, so as to illustrate insertion of an arm into the hollow opening of the living body insert portion. FIG. 4 is a schematic diagram showing a posture for measurement taken after the application thereof. It should be noted that these figures assumes that a blood pressure value is measured from the right arm.

As shown in FIG. 3, upon measurement of a blood pressure value with blood pressure monitor 100 of the present embodiment, main unit 110 of blood pressure monitor 100 is placed on a desk 210 corresponding to a horizontal placement table, and subject 300 sits on a chair 220. Pressing down unlocking button 146, subject 300 moves living body insert portion 140 in the direction shown by arrow A1 in the figure. Subject 300 then inserts the right hand into hollow opening 150 of living body insert portion 140, while gripping handle 144 provided at living body insert portion casing 142 of blood pressure monitor 100 with the left hand to adjust the inclination angle of living body insert portion 140. Subject 300 inserts the right hand to the further depth of hollow opening 150, until a forearm 310 and then an upper arm 320 faces cuff 145 provided in living body insert portion 140. With slightly bending the elbow of the right arm inserted in hollow opening 150, subject 300 rests the elbow on elbow rest 119 provided at the upper surface of main unit 110, to thereby take the posture for measurement as shown in FIG. 4.

During the procedure for applying cuff 145, the inclination angle of living body insert portion 140 changes in accordance with the inclination angle of the right arm. Specifically, living body insert portion 140 turns following the movement of the right hand, as the right hand and then the right arm inserted in hollow opening 150 of living body insert portion 140 contact the inner peripheral surface of hollow opening 150. For example, at the stage where the right hand is inserted, it is preferable that living body insert portion 140 is turned in advance to the position corresponding to the maximum moved state (described below) as shown in FIG. 3 or closer thereto, to reduce the burden imposed on the subject. At the subsequent stage where the right hand and then the right arm is further inserted, however, it is preferable that living body insert portion 140 pivotally moves in the direction shown by an arrow A2 as shown in FIG. 4 in accordance with the movement of the right hand and arm.

Figure 5:
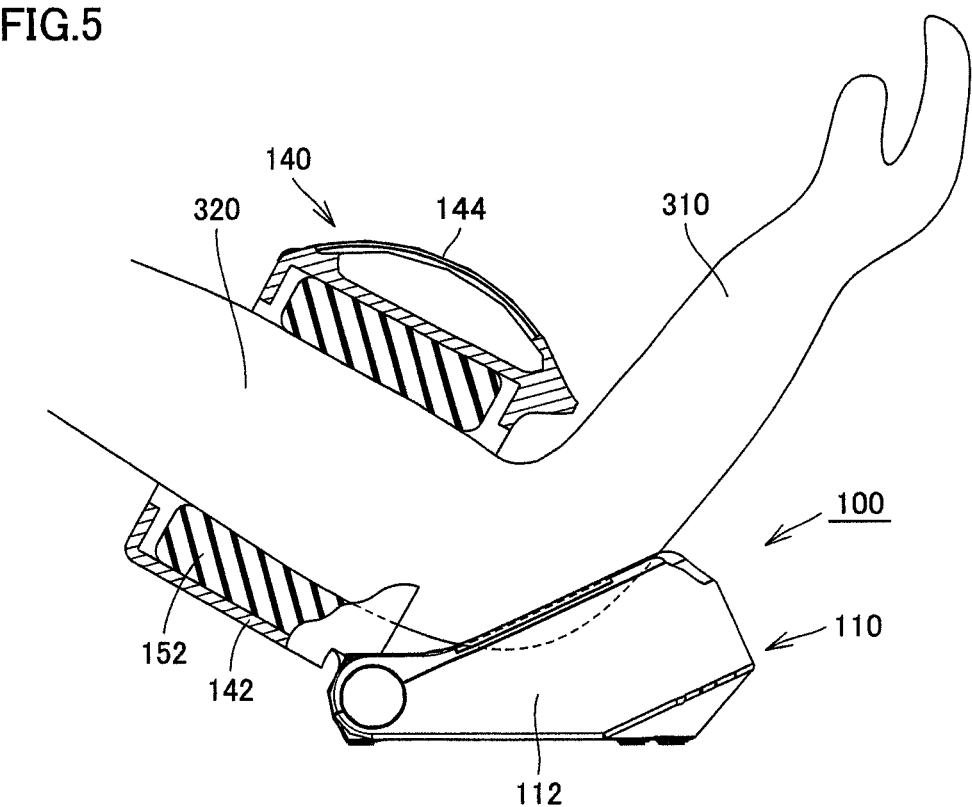
FIG. 5 is a schematic cross sectional view showing a posture for measurement when measuring a blood pressure value using the blood pressure monitor of each embodiment of the present invention.

FIG. 5 is a schematic cross sectional view showing a posture for measurement when measuring a blood pressure value using blood pressure monitor 100 of the first embodiment of the present invention. As shown in FIG. 5, in blood pressure monitor 100 of the present embodiment, arterial pressure pulse waves caused in the artery located within upper arm 320 by inflation/deflation of a living body pressing air bag 152 are detected to measure the blood pressure value. During the measurement as well, living body insert portion 140 rotates following the movement of the upper arm. This ensures good contact between cuff 145 and the living body, and measurement with high accuracy becomes possible.

Meanwhile, as shown in FIG. 3, the back of subject 300 needs to be straight so that heart 330 is positioned as high as the height of upper arm 320, which is a measurement site. In this way, a blood pressure value can be measured accurately.

However, according to the above-described configuration of blood pressure monitor 100 of the first embodiment, since living body insert portion 140 is movable toward main unit 110, a blood pressure value can be measured irrespective of postures as long as upper arm 320 is inserted into living body insert portion 140. Hence, subject 300 may measure it with an unnatural posture (of inclining forward or the like) or with different postures every time, if he/she does not know what posture should be taken for measurement. In such cases, accuracy in measurement cannot be maintained. To accommodate this, blood pressure monitor 100 of the present embodiment performs control for leading subject 300 into a posture that should be taken for measurement. Specific processing for this will be described below.

Figure 6:
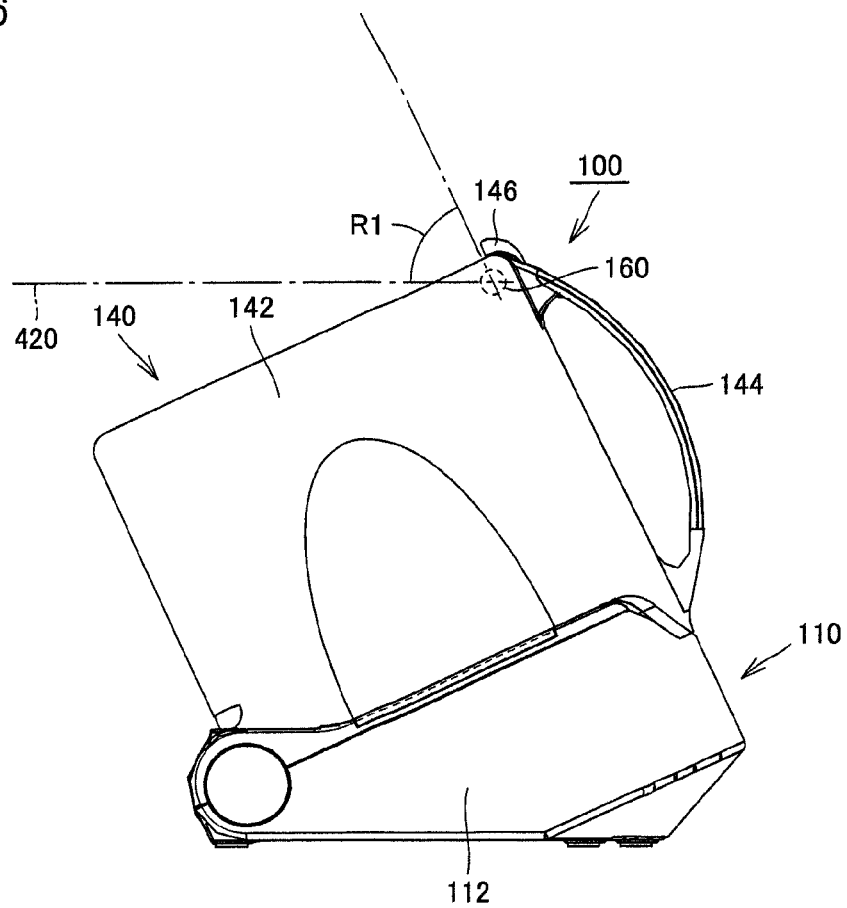
FIG. 6 shows a rest state in which the living body insert portion casing is located on the main unit casing in the blood pressure monitor of each embodiment of the present invention.
Figure 7:
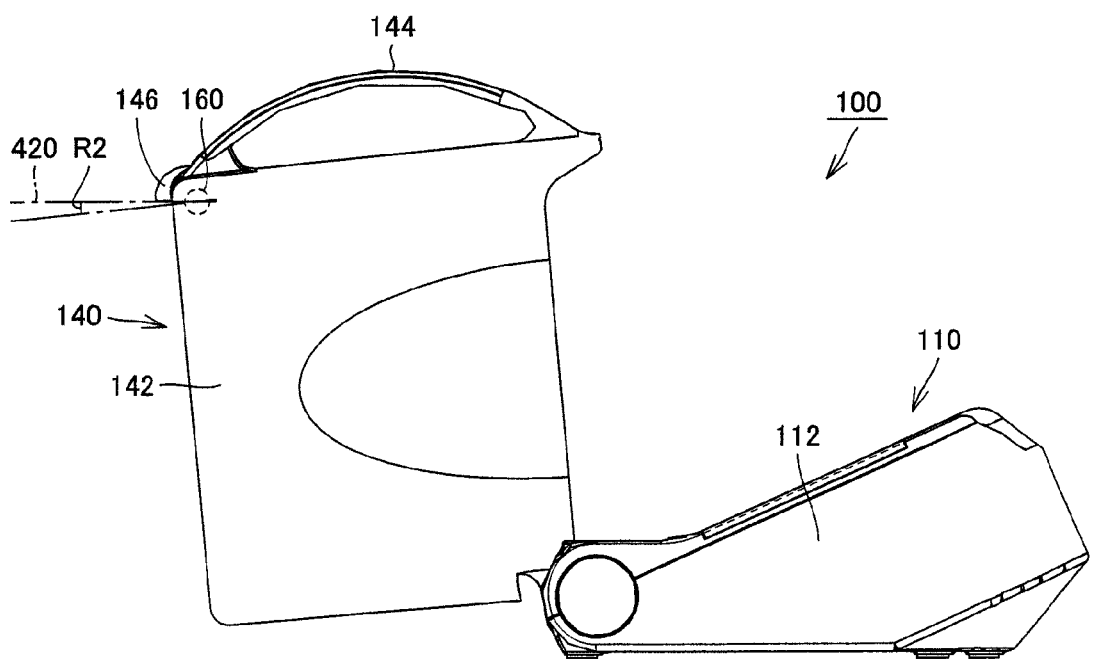
FIG. 7 shows a maximum moved state in which the living body insert portion casing of the blood pressure monitor of each embodiment of the present invention is pivoted to move toward the subject as much as possible.

FIGS. 6 and 7 are right side views of the blood pressure monitor of the present embodiment. FIG. 6 shows a rest state in which living body insert portion casing 142 is rested on main unit casing 112. FIG. 7 shows a maximum moved state in which living body insert portion casing 142 is pivotally moved toward the subject as much as possible.

As described above, in blood pressure monitor 100 of the present embodiment, main unit casing 112 and living body insert portion casing 142 are separated from each other. Hinge portion 141 connects main unit casing 112 and living body insert portion casing 142 thus separated from each other.

As shown in FIG. 6, when blood pressure monitor 100 is in the rest state (non-use state), living body insert portion casing 142 is rested on main unit casing 112. The upper surface of main unit casing 112 is formed slopewise in advance such that when it is placed on a horizontal placement table such as a desk, it is arranged at a prescribed angle with respect to horizontal plane 420. Living body insert portion casing 142 is rested on main unit casing 112 in such a manner that the axis line of hollow opening 150 of living body insert portion casing 142 is orthogonal to the upper surface of main unit casing 112 thus inclined. Here, the inclination angle of living body insert portion casing 142 with respect to horizontal plane 420 in the rest state is represented as R1.

As shown in FIG. 7, when the subject pivots and moves living body insert portion casing 142 to bring it into the maximum moved state (state in which it is pivoted to be positioned closest to the subject in a pivotally movable range that restricts the pivotal movement therewithin), living body insert portion casing 142 thus moved comes closer to the subject relative to main unit casing 112. In this state, the axis line of hollow opening 150 is tilted to the extent slightly beyond the state parallel to horizontal plane 420. Here, the inclination angle of living body insert portion casing 142 with respect to horizontal plane 420 in the maximum moved state is represented as R2.

In blood pressure monitor 100 of the present embodiment, living body insert portion casing 142 can pivotally move freely, by an operation of the subject, within the movable range from the position corresponding to the rest state shown in FIG. 6 to the position corresponding to the maximum moved state shown in FIG. 7. In other words, living body insert portion casing 142 pivotally moves from the position in the rest state to approach the subject within the range of the angle (R1+R2).

As the pivot connection mechanism allowing living body insert portion casing 142 to pivot, a mechanism disclosed in Japanese Patent Laying-Open No. 2003-93355 (patent document 1) is used, for example.

Figure 8:
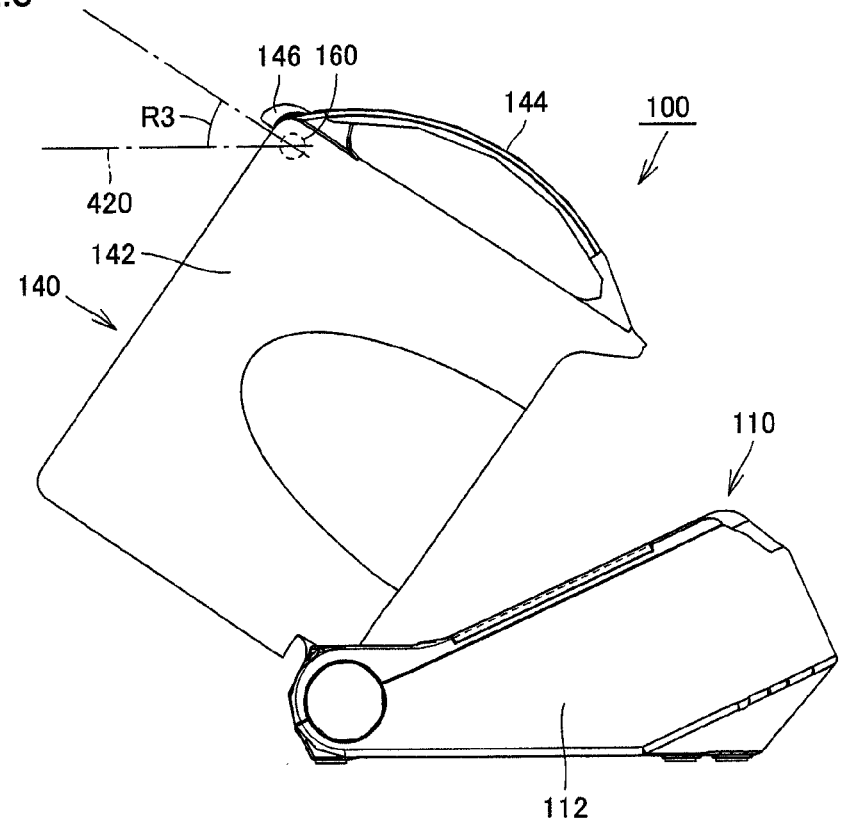
FIG. 8 shows a state in which the living body insert portion casing is located at a minimum moved position within a recommended inclination range in the blood pressure monitor of each embodiment of the present invention.
Figure 9:
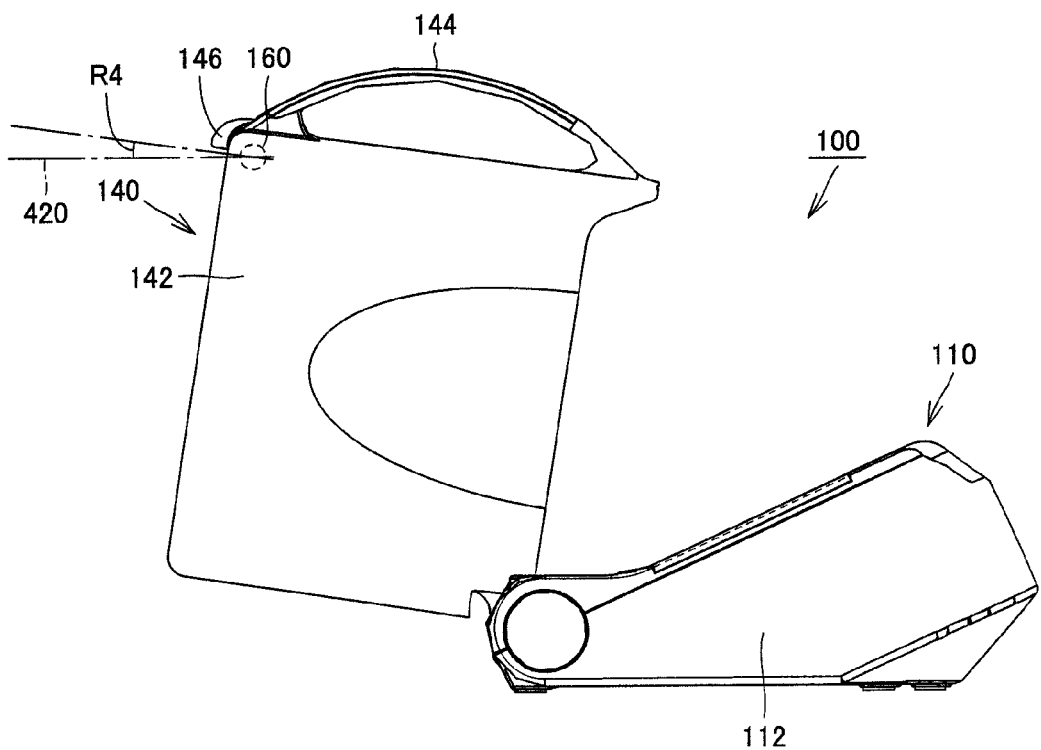
FIG. 9 shows a state in which the living body insert portion casing is located at a maximum moved position within the recommended inclination range in the blood pressure monitor of each embodiment of the present invention.

FIGS. 8 and 9 are right side views of the blood pressure monitor of the present embodiment. To realize the posture for measurement that keeps the difference between the height of the upper arm around which cuff 145 is wound and the height of the heart within a small range, an optimal range for the inclination angle of the upper arm inserted into hollow opening 150 of living body insert portion 140 is necessarily derived. The optimal range for the inclination angle of the upper arm corresponds to the inclination level of living body insert portion casing 142 at the time of measurement, and as a result, a recommended inclination range (optimal measurement range) of living body insert portion casing 142 is determined.

FIG. 8 shows the state where living body insert portion casing 142 is in a minimum moved position within the recommended inclination range enabling accurate measurement of the blood pressure value. Here, the inclination angle of living body insert portion casing 142 with respect to horizontal plane 420 in this state is represented as R3.

FIG. 9 shows the state where living body insert portion casing 142 is in a maximum moved position within the recommended inclination range enabling accurate measurement of the blood pressure value. Here, the inclination angle of living body insert portion casing 142 with respect to horizontal plane 420 in this state is represented as R4.

Figure 10:
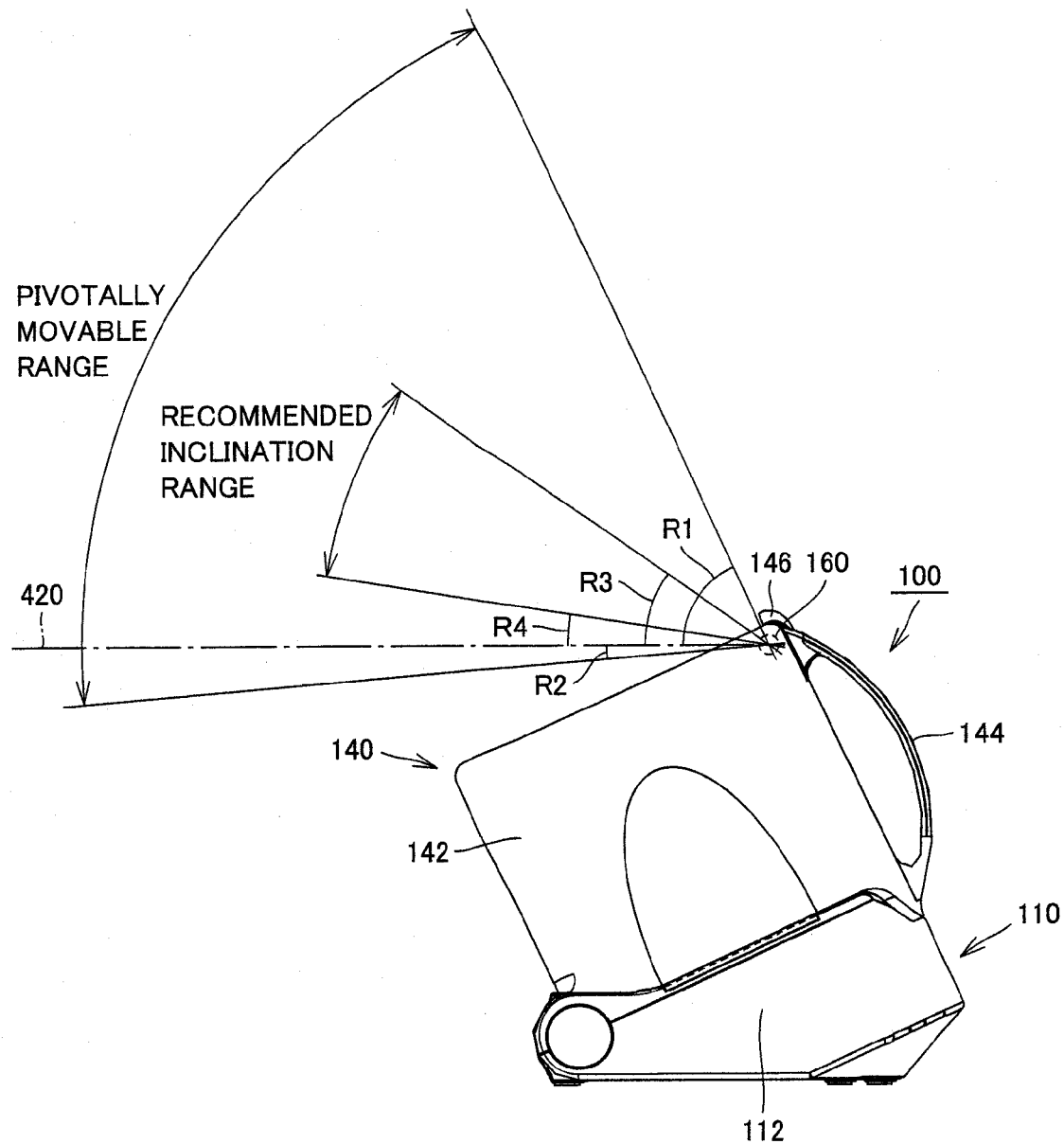
FIG. 10 shows a relation between a pivotally movable range and the recommended inclination range in the blood pressure monitor of each embodiment of the present invention.

FIG. 10 shows a relation between the pivotally movable range (movable range) and the recommended inclination range in blood pressure monitor 100 of the first embodiment of the present invention. As shown in FIG. 10, in blood pressure monitor 100 of the present embodiment, living body insert portion casing 142 freely turns within a movable range that is defined by inclination angles R1 and R2 shown in the figure. On the other hand, the recommended inclination range of living body insert portion casing 142 corresponds to a range obtained by subtracting inclination angle R4 from inclination angle R3 shown in the figure. The recommended inclination range is included in the movable range, and has the inclination angle with respect to horizontal plane 420 preferably within the range from 15° to 45°.

As to Configuration

Figure 11:
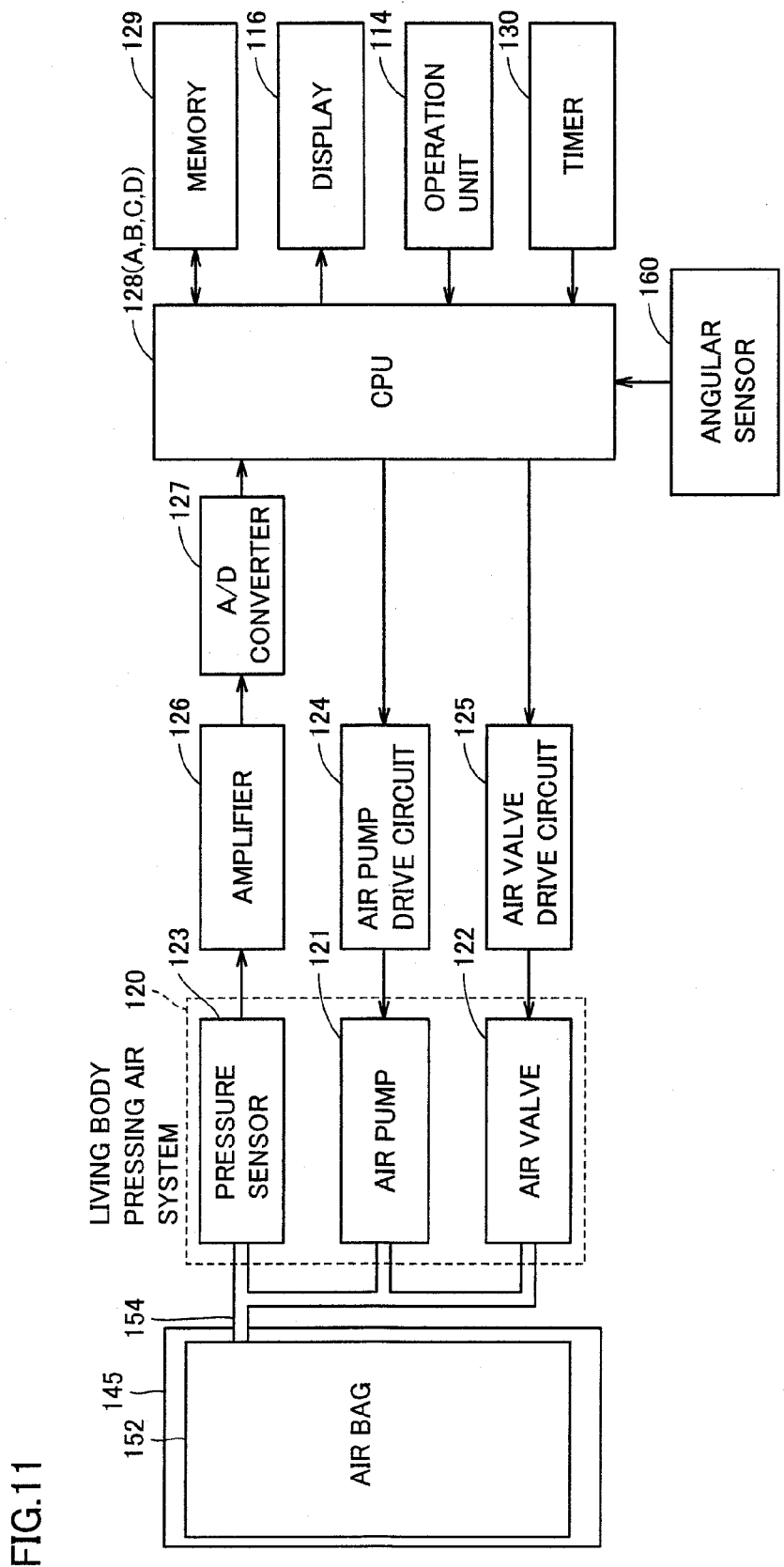
FIG. 11 is a hardware block diagram showing a configuration of the blood pressure monitor of each embodiment of the present invention.

FIG. 11 is a hardware block diagram showing a configuration of blood pressure monitor 100 of the first embodiment of the present invention.

As shown in FIG. 11, in addition to control portion 114 and display portion 116, blood pressure monitor 100 includes living body pressing air bag 152 provided within cuff 145; a pressure sensor 123 for detecting pressure in the bladder of living body pressing air bag 152 (hereinafter referred to as "cuff pressure"); an amplifier 126 for amplifying a signal detected by pressure sensor 123; an A/D converter 127 for converting an amplified analog signal into a digital signal; an air pump 121 and an air valve 122 both for adjusting the level of cuff pressure; an air pump drive circuit 124 for driving air pump 121; an air valve drive circuit 125 for adjusting how air valve 122 opens and closes in degree; a CPU (Central Processing Unit) 128 for controlling and monitoring each unit in a centralized manner; a memory 129 for storing various types of data and program; a timer 130 operative to measure time and output measured-time data; and angular sensor 160 for detecting an inclination angle of living body insert portion casing 142.

As such, living body pressing air bag 152 is connected by air tube 154 to a living body pressing air system 120 including air pump 121, air valve 122, and pressure sensor 123.

CPU 128 is connected to A/D converter 127, air pump drive circuit 124, air valve drive circuit 125, memory 129, display portion 116, control portion 114, timer 130, and angular sensor 160.

In blood pressure monitor 100 of the present embodiment, all the blocks except for living body pressing air bag 152, pressure sensor 123, and angular sensor 160 are provided at main unit 110, and accommodated in main unit casing 112. Living body pressing air bag 152, pressure sensor 123, and angular sensor 160 are provided at living body insert portion 140, and accommodated in living body insert portion casing 142. Living body pressing air bag 152, air pump 121, and air valve 122 are connected via a flexible air tube, and pressure sensor 123 and amplifier 126 are connected via a flexible signal line. Further, angular sensor 160 and CPU 128 are connected via a flexible signal line. The flexible air tube and the flexible signal lines used to connect the components accommodated in main unit casing 112 and those accommodated in living body insert portion casing 142 can follow the pivotal movement of living body insert portion casing 142 to enable injection/discharge of the air and transmission/reception of the signals.

Angular sensor 160 is representatively an acceleration sensor and detects an inclination angle of living body insert portion casing 142 relative to the horizontal plane. Angular sensor 160 may detect an inclination angle of living body insert portion casing 142 relative to main unit casing 112. Alternatively, the inclination angle may be detected using various switches. A tact switch, a rotary switch, a switch employing variable resistance, and the like can be used to detect the inclination angle of living body insert portion casing 142 indirectly from the amount of movement of living body insert portion casing 142.

It should be noted that the location in which angular sensor 160 is provided is not limited to the upper portion of living body insert portion casing 142. For example, it may be provided at hinge portion 141. Further, angular sensor 160 may detect a degree of levelness of the bottom surface of main unit casing 112 (surface making contact with the placement table such as a desk). In this case, when it is determined that the bottom surface of main unit casing 112 is not horizontal, CPU 128 may be adapted to notify (display, for example) that it is not horizontal.

To provide various types of notification to the subject, blood pressure monitor 100 may be further provided with a buzzer or the like.

Figure 12:
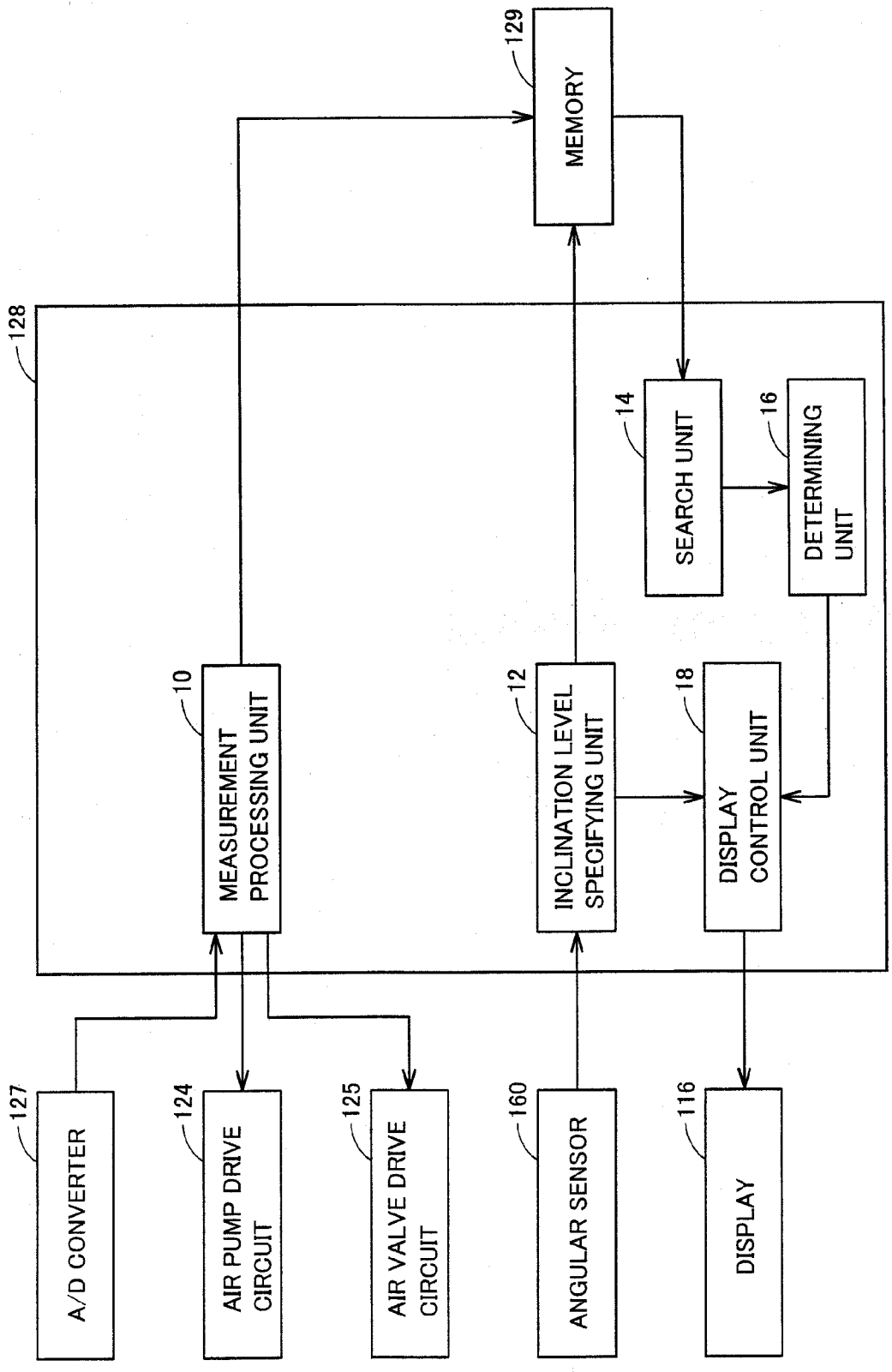
FIG. 12 is a function block diagram showing a functional configuration of the blood pressure monitor of the first embodiment of the present invention.

FIG. 12 is a functional block diagram showing a functional configuration of blood pressure monitor 100 of the first embodiment of the present invention.

Referring to FIG. 12, CPU 128 includes a measurement processing unit 10 for performing processing for measuring the blood pressure of the subject, an inclination level specifying unit 12, a search unit 14, a determining unit 16, and a display control unit 18 for generating a signal for display on display portion 116.

Inclination level specifying unit 12 specifies a current inclination level of living body insert portion casing 142 based on a result of detection by angular sensor 160. More specifically, based on a result of detection by angular sensor 160, inclination level specifying unit 12 specifies a current inclination level among a predetermined number of inclination levels.

Here, the "inclination level" of living body insert portion casing 142 refers to a degree of inclination of living body insert portion casing 142. For example, it indicates a magnitude of inclination determined from an inclination angle relative to the horizontal plane, an inclination angle relative to main unit casing 112, or an amount of movement of living body insert portion casing 142 from main unit casing 112.

Further, the predetermined number of inclination levels correspond to the predetermined number of ranges into which the movable range of living body insert portion casing 142 is divided. Namely, for example, when ten inclination levels (levels 1, 2, ..., 10) has been set in advance, the movable range of living body insert portion casing 142 is divided by 10. It should be noted that the number of inclination levels is not particularly limited but is preferably the number corresponding to ranges of angles obtained by dividing the recommended inclination range into at least two.

Upon completion of measurement, data of the inclination level specified by inclination level specifying unit 12 is recorded onto memory 129 in association with blood pressure data measured by measurement processing unit 10. Thus, for each measurement, memory 129 stores blood pressure data and data of an inclination level in association with each other.

Before and/or during measurement, notification of at least one past inclination level of the plurality of inclination levels recorded in memory 129 and the current inclination level is presented in association with each other. In the present embodiment, display control unit 18 generates a signal for displaying the most recent inclination level recorded in memory 129 and the current inclination level specified by inclination level specifying unit 12, in association with each other. The signal thus generated by display control unit 18 is sent to display portion 116. In this way, the current inclination level and the most recent inclination level of past are displayed on display portion 116 in association with each other.

In the present embodiment, they are displayed (notification thereof is presented) only when the most recent inclination level falls within the above-described recommended inclination range.

Specifically, search unit 14 searches for and reads out the data of the most recent inclination level among the data of the plurality of inclination levels recorded in memory 129. Determining unit 16 determines whether or not the most recent inclination level thus read out falls within the above-described recommended inclination range. Only when the most recent inclination level is within the recommended inclination range, the data of the inclination level is output to display control unit 18.

Thus, when the most recent inclination level is out of the recommended inclination range, display control unit 18 generates a signal for displaying only the current inclination level.

An operation of each of the blocks shown in FIG. 12 may be implemented by executing software stored in memory 129 or at least one of them may be implemented by hardware.

Figure 13:
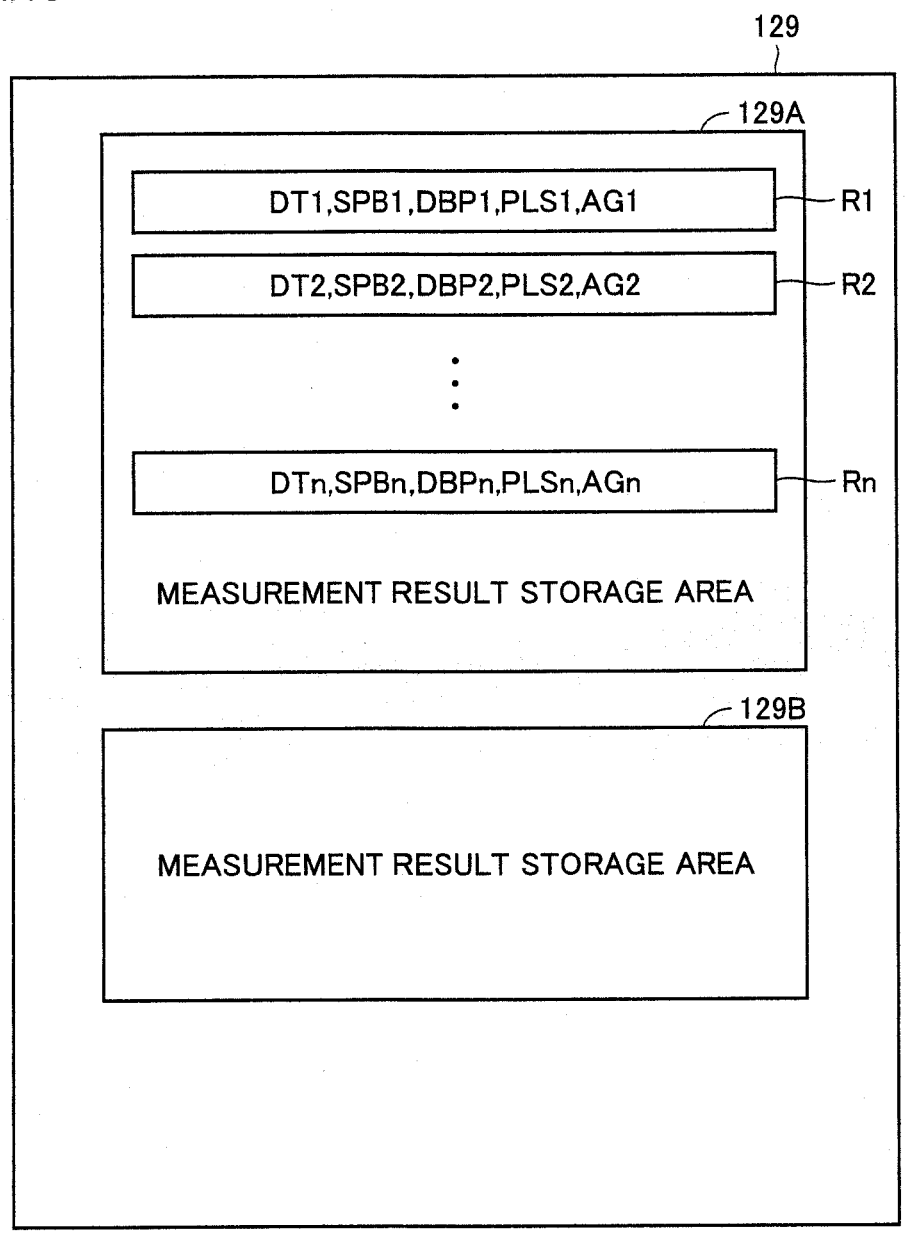
FIG. 13 shows one exemplary data structure of a memory in the blood pressure monitor of each embodiment of the present invention.

FIG. 13 shows one exemplary data structure in memory 129 of blood pressure monitor 100 of the first embodiment of the present invention.

Referring to FIG. 13, memory 129 includes measurement result storage areas 129A, 129B, . . . for respective users (subjects). Measurement result storage area 129A stores measurement data, such as blood pressure data, and data of an inclination level in pair based on a record R as a unit.

Specifically, in a record Ri (i=1, 2, 3, . . . , n), measurement date/time data DTi, systolic blood pressure data SBPi, diastolic blood pressure data DBPi, pulse rate data PLSi, and inclination level data AGi are stored. The same hold true for the data structure in the other measurement result storage area 129B.

In the present embodiment, the measurement data and the inclination level data are stored in pair but they may be stored in a different manner as long as these data are associated with each other. Thus, as long as the measurement data and the inclination level data are associated with each other, the area in which the measurement data are stored and the area in which the inclination level data are stored may be provided separately.

As to Operation

The following describes a specific operation of blood pressure monitor 100 of the embodiment of the present invention.

Figure 14:
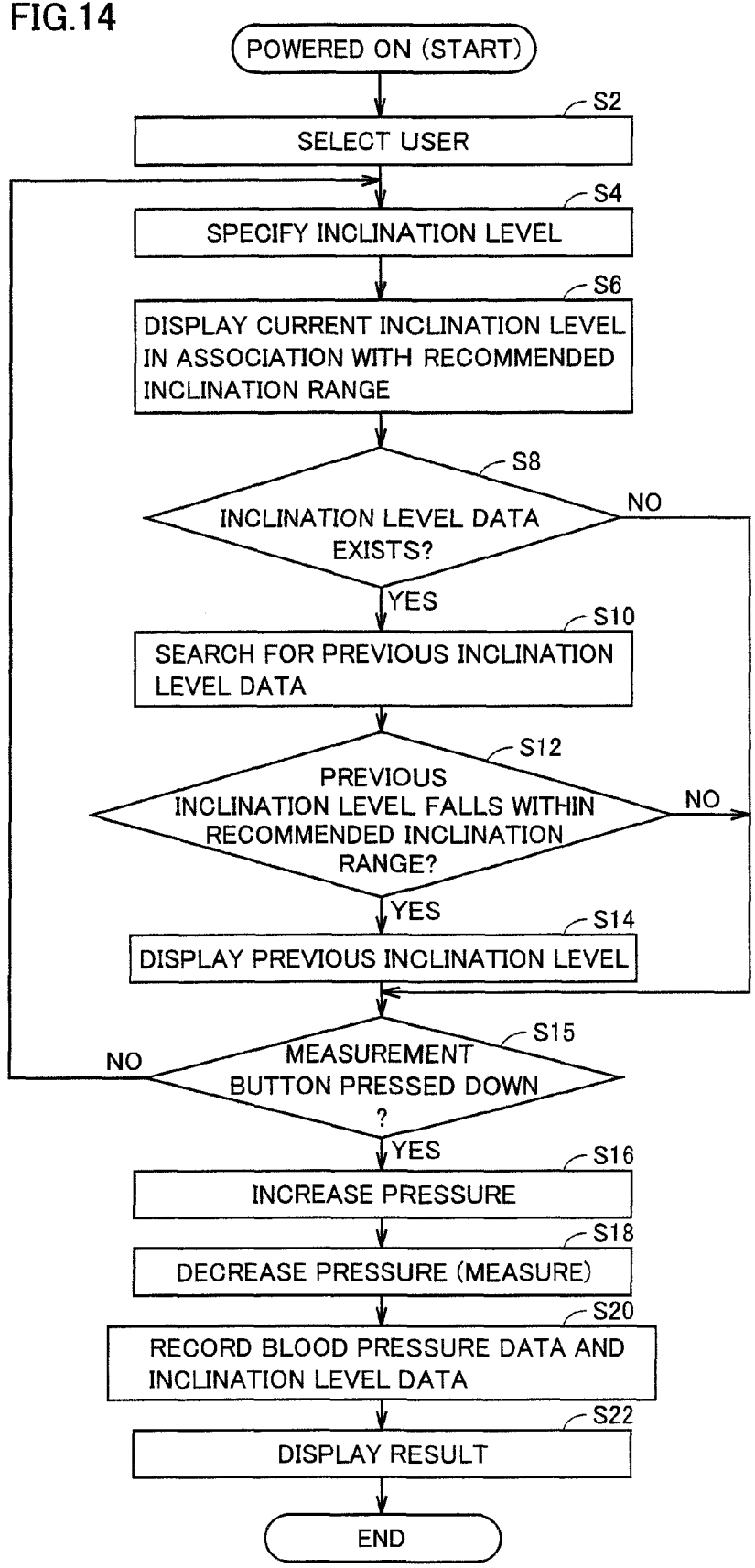
FIG. 14 is a flowchart showing blood pressure measuring/recording processing performed in a blood pressure monitor of a first embodiment of the present invention.

FIG. 14 is a flowchart showing blood pressure measuring/recording processing performed by blood pressure monitor 100 of the first embodiment of the present invention. The processing shown in the flowchart of FIG. 14 is implemented by a program stored in advance in memory 129. CPU 128 reads out and executes the program to implement functions of the blood pressure measuring/recording processing. The blood pressure measuring/recording processing is started when powered on based on an instruction from a subject.

Referring to FIG. 14, when powered on, CPU 128 first receives a selection of a user based on an instruction of a subject (step S2). The received information about the user (for example, a user A) is temporarily stored in an internal memory.

Then, based on an output of angular sensor 160, a current inclination level is specified (step S4). The inclination level is specified based on the output from angular sensor 160 and a predetermined computational expression. Alternatively, the current inclination level may be specified based on an inclination angle detected by angular sensor 160 and an association table which is stored in memory 129 and in which each inclination level and a range of angles (inclination angles) are associated with each other.

When the inclination level is specified, display control unit 18 causes the current inclination level to be displayed in a block set indicating a movable range of living body insert portion casing 142 (step S6). The current inclination level is preferably displayed (in the block set) in association with the recommended inclination range. The block set will be described in detail below.

Then, it is determined whether or not inclination level data is stored in memory 129 (step S8). When it is determined that inclination level data is stored (YES in step S8), the processing goes to step S10. On the other hand, when it is determined that inclination level data is not stored (NO in step S8), the processing goes to step S15.

In step S10, search unit 14 searches for and reads out the previous (most recent) inclination level data stored in measurement result storage area 129A of memory 129.

Thereafter, determining unit 16 determines whether or not the previous inclination level data thus read out falls within the recommended inclination range (step S12). When the inclination level data is within the recommended inclination range (YES in step S12), the processing goes to step S14. On the other hand, when it is determined that the inclination level data is out of the recommended inclination range (NO in step S12), the processing goes to step S15.

In step S14, display control unit 18 causes the previous inclination level to be displayed in association with the current inclination level. Namely, display control unit 18 performs processing to further indicate the previous inclination level in the block set (in which the current inclination level is presented) displayed in step S6. Accordingly, the subject can adjust the posture for measurement to come close to the previous posture for measurement. In this way, the same posture (the same inclination level) can be taken for each measurement. Furthermore, this allows improved accuracy in the measurement. When the processing in step S14 is ended, the processing goes to step S15.

In step S15, CPU 128 determines whether or not a measurement button is pressed down. In other words, CPU 128 determines based on a signal from control portion 114 whether or not an instruction to start measurement is received from the user. When it is not detected during a fixed period of time that an instruction to start measurement is input (NO in step S15), the processing goes back to step S4. It should be noted that in the second time or later of processing, the processing in each of steps S8-S12 (preprocessing for "display of the previous inclination level") may not be performed. Thus, once the previous inclination level is displayed, the previous inclination level is kept on being displayed until it is detected that an instruction to start measurement is input.

In step S15, when it is detected that an instruction to start measurement is input (YES in step S15), the processing goes to step S16.

In step S16, measurement processing unit 10 starts to drive air pump drive circuit 124 to perform a pressurization process of gradually increasing the cuff pressure of living body pressing air bag 152. When the cuff pressure reaches a predetermined level for measurement of blood pressure in the process of gradually increasing pressure, measurement processing unit 10 stops air pump drive circuit 124. Then, measurement processing unit 10 controls air valve drive circuit 125 to gradually decrease the cuff pressure, and measures blood pressure (systolic blood pressure and diastolic blood pressure) and pulse rate in accordance with a known procedure (step S18). Specifically, in the process of gradually decreasing the cuff pressure, measurement processing unit 10 extracts pulse wave information based on a signal obtained from A/D converter 127. In accordance with the pulse wave information thus extracted, the blood pressure is calculated.

The above description assumes that the processing in each of steps S4, S6 and the processing in each of steps S8-S14 are performed in series, but they may be performed in parallel. Further, in the case of serial processing, they can be performed in any order. Further, in serial processing and parallel processing, the processing in step S6 and the processing in step S14 may be integrated.

Further, during the blood pressure measurement processing in steps S16 and S18, both the current inclination level and the previous inclination level are preferably displayed on display portion 116. In other words, during the blood pressure measurement processing, the processing in steps S4 and S6 and the processing in step S14 are preferably performed in parallel. This allows the subject to keep stable posture during measurement.

In the present embodiment, the blood pressure is measured in the process of gradually decreasing the cuff pressure, but the blood pressure may be measured in the process of increasing the cuff pressure.

When the measurement of blood pressure is ended, CPU 128 associates the measured blood pressure data (and pulse rate data) with the inclination level data, and records them onto memory 129 (step S20). More specifically, in measurement result storage area 129A corresponding to the user (user A) selected in step S2, measurement date/time data DTn, systolic blood pressure data SBPn, diastolic blood pressure data DBPn, pulse rate data PLSn, and inclination level data AGn are stored.

Here, the inclination level data stored in measurement result storage area 129A is inclination level data obtained upon the measurement of blood pressure, and is preferably indicative of the inclination level specified in step S18 based on the signal sent from angular sensor 160.

Finally, display control unit 18 causes a result of the measurement to be displayed on display portion 116 (step S22).

It should be noted that the processing in step S20 and the processing in step S22 may be performed in an inverse order or in parallel.

Exemplary Display of Blood Pressure Measuring/Recording Processing

Figure 15:
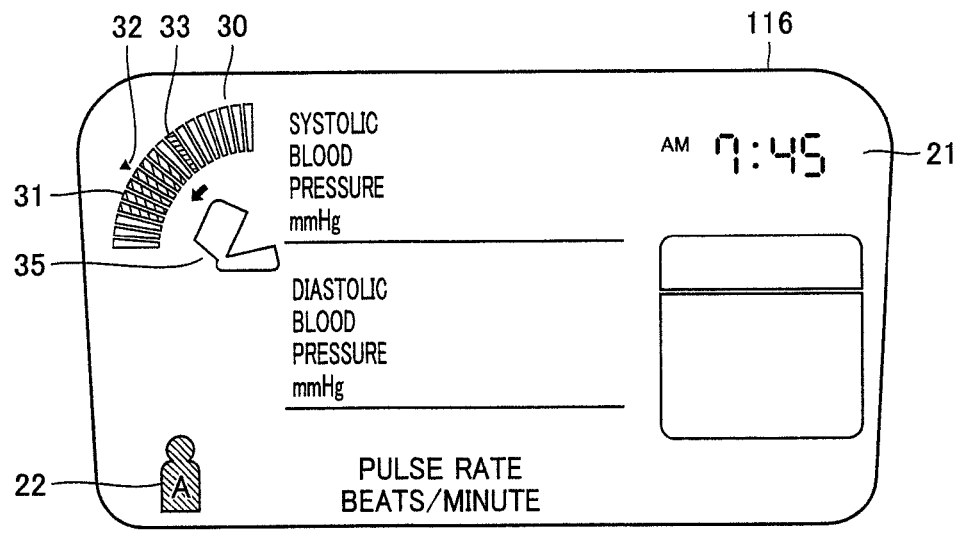
FIG. 15 shows one exemplary screen displayed in a step S14 of FIG. 14.
Figure 16:
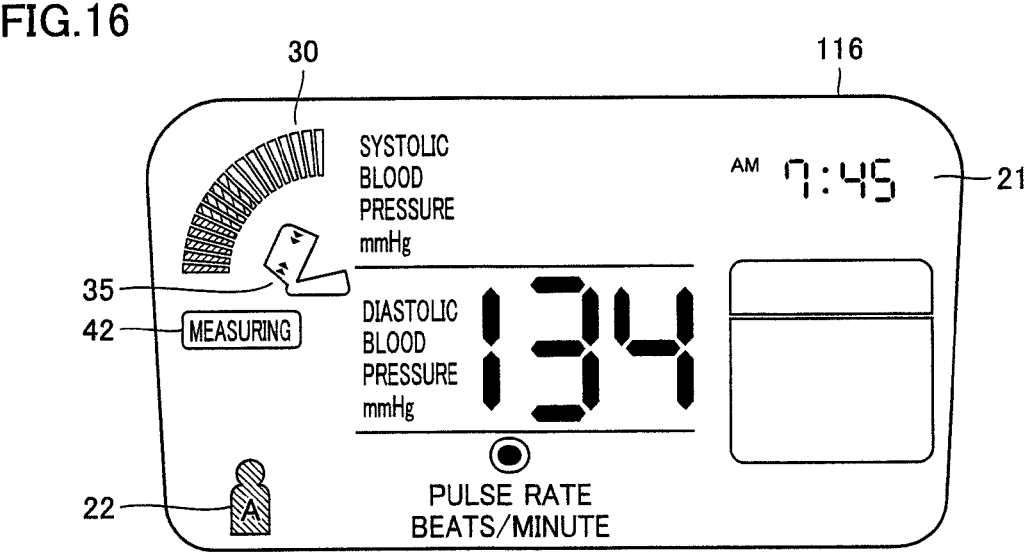
FIG. 16 shows one exemplary screen displayed in a step S18 of FIG. 14.
Figure 17:
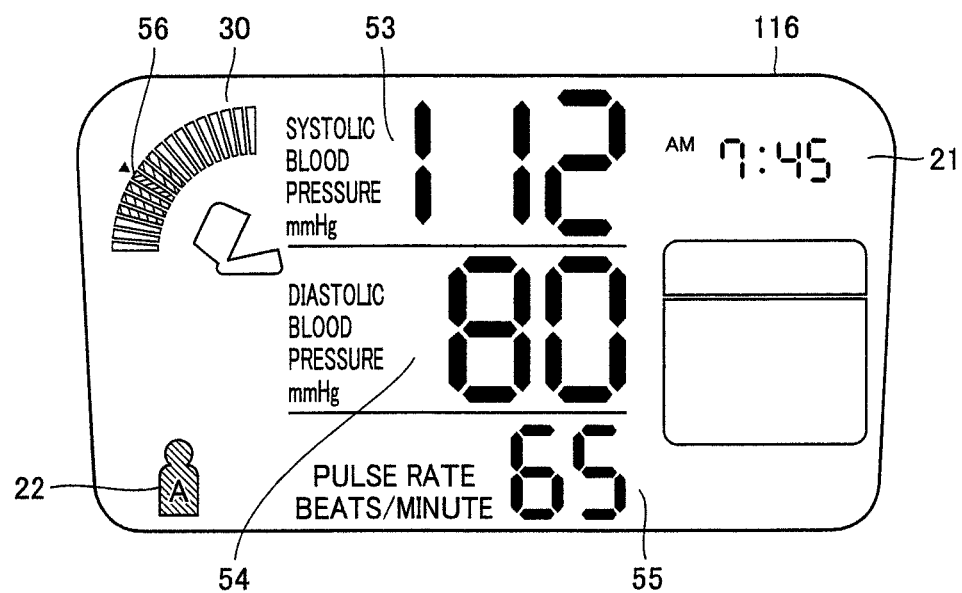
FIG. 17 shows one exemplary screen displaying a result of measurement in step S22 of FIG. 14.

The following describes an exemplary screen displayed on display portion 116 in the above-described blood pressure measuring/recording processing, with reference to FIGS. 15-17.

FIG. 15 shows one exemplary screen displayed in step S14 of FIG. 14.

Referring to FIG. 15, display portion 116 displays current time 21 measured by timer 130, user information 22 selected in step S2, block set 30, and a pictogram 35 schematically representing a relation between main unit casing 112 and living body insert portion casing 142 in blood pressure monitor 100.

Block set 30 includes the predetermined number of blocks, which correspond to the predetermined number of inclination levels respectively. Block set 30 is displayed above pictogram 35 in the form of an arc. The plurality of blocks included in block set 30 are displayed corresponding to the movable range of living body insert portion casing 142 indicated in pictogram 35. It should be noted that each block may be a segment.

In the present embodiment, among the blocks of block set 30, blocks within the recommended inclination range are displayed in a manner different from blocks outside the recommended inclination range. For example, the blocks outside the recommended inclination range are displayed in white, and the blocks within the recommended inclination range are displayed in yellow. In this way, even when the subject measures blood pressure for the first time, the subject can readily know in what range living body insert portion casing 142 should be inclined, i.e., what posture should be taken for measurement.

In the present embodiment, a predetermined mark such as a triangular mark 32 is displayed at a block corresponding to the current inclination level, among the blocks of block set 30.

Further, a block 33 corresponding to the previous inclination level among the blocks of block set 30 is displayed in a manner different from the other blocks. For example, the block corresponding to the previous inclination level is displayed in red.

Instead of using triangular mark 32 to indicate the block corresponding to the current inclination level, the block corresponding to the current inclination level may be displayed, for example, in blue. In this case, when the previous inclination level and the current inclination level are matched with each other, a block at which they are matched may be displayed in, for example, green. Alternatively, instead of displaying in red the block corresponding to the previous inclination level, some mark may be added for the block corresponding to the current inclination level.

Further, as shown in FIG. 15, when the previous inclination level and the current inclination level are not matched with each other, a direction in which living body insert portion casing 142 is inclined may be indicated by an arrow or the like in the vicinity of pictogram 35 in order to lead the current inclination level to come close to the previous inclination level. In this way, the subject can see and recognize which direction living body insert portion casing 142 should be actually inclined in (the direction toward the subject or the opposite direction).

FIG. 16 shows one exemplary screen displayed in step S18 of FIG. 14.

Referring to FIG. 16, display portion 116 displays information 42 indicating that blood pressure is being measured. Alternatively, the displayed plurality of blocks of block set 30 may be fully colored sequentially from the one located at the bottom so as to indicate that measurement is going on. Alternatively, a plurality of triangular marks indicating states of increasing/decreasing pressure may be displayed at pictogram 35. It should be noted that during measurement, a mark is preferably rendered to a block corresponding to the current inclination level.

FIG. 17 shows one exemplary screen displayed in step S22 of FIG. 14 to present the result of measurement.

Referring to FIG. 17, in addition to current time 21 and user information 22, display portion 116 displays a systolic blood pressure value 53, a diastolic blood pressure value 54, and a pulse rate 55. A block 56 corresponding to the inclination level of the current measurement among the blocks of block set 30 is displayed in a manner different from the other blocks.

As such, according to the present embodiment, upon the measurement, the information about the current inclination level and the information about the previous inclination level are presented on block set 30, thereby leading the subject into the same posture as the previous posture. In other words, the subject can be conscious of the previous inclination level in deciding a posture to be taken (angle of insertion of the upper arm) for measurement.

Furthermore, this allows stable measurement for each time, thus achieving accurate ascertainment of changes in blood pressure value. As a result, appropriateness of long-term changes in blood pressure can be determined.

Meanwhile, in the present embodiment, the current inclination level and the previous inclination level are displayed in association with the recommended inclination range of living body insert portion casing 142. Hence, the subject can take such a posture that the current inclination level is included in the recommended inclination range for each time, thereby eliminating influences of the difference (deviation) in posture over measurement values.

Further, in the present embodiment, when the previous inclination level falls out of the recommended inclination range, it is not displayed. Thus, if the subject accidentally (by chance) takes such a posture that the inclination level falls out of the recommended inclination range, only the current inclination level is displayed. Hence, even if accuracy in measurement is decreased once, the subject can reproduce the high accuracy in measurement by taking such a posture that the current inclination level falls within the recommended inclination range.

In the present embodiment, the information about the recommended inclination range as well as the information about the current inclination level and the previous inclination level are displayed on block set 30. However, the present invention is not limited to such a manner of display, and, for example, each inclination level may be simply indicated by a numerical value, a symbol, or the like.

Exemplary Display of Measurement Record Data

In the present embodiment, CPU 128 may be adapted to read out measurement record data (measurement result data) stored in measurement result storage areas 129A, B of memory 129 when receiving from control portion 114 an instruction for displaying (reading out) the record data. In this case, display control unit 18 controls display portion 116 to display the measurement record data thus read out.

Each of FIGS. 18(A), (B) shows an exemplary display screen of a measurement record upon displaying the measurement record data in the first embodiment of the present invention.

As shown in FIG. 18(A), based on the readout measurement record data, display portion 116 displays user information 52, systolic blood pressure 53, diastolic blood pressure value 54, and pulse rate 55, as well as inclination level 56 in block set 30. In FIG. 18(A), current time 51 is displayed but a date and time upon the measurement may be displayed.

Further, a result of determination of a blood pressure value (as to a predetermined item thereof) by CPU 128 may be displayed in predetermined areas 62, 63. In FIG. 18(A), nothing is displayed in area 62 whereas a "high" mark 61 is displayed in the vicinity of block set 30 to indicate that the blood pressure is high. In this way, it can be recognized that the displayed measurement data is indicative of high blood pressure unrelated to morning surge. It should be noted that the present invention is not limited to such display and, for example, an LED, which is lit up to indicate that blood pressure is high, may be provided below pictogram. In area 63, it is displayed that the data was measured in morning, was around an average value of blood pressure measured in morning, and the like.

In contrast, referring to FIG. 18(B), "MORNING SURGE" is displayed in area 62 whereas it is displayed in area 63 that the data was measured at night, was around an average value of blood pressure measured at night, and the like.

As such, when displaying the information about morning surge and the like, it is assumed that CPU 128 further has a function of determining whether the blood pressure results from morning surge or is a mere high blood pressure, or the like, based on a predetermined computational expression or a predetermined association table. Further, in such a case, similar determination and display may be performed upon displaying a result of measurement in step S22 of FIG. 14.

As described above, in the case of displaying the measurement record data, the measurement record data is displayed together with the data of inclination level upon the measurement. Therefore, the subject can recognize reliability of the displayed measurement data, or the like. This also facilitates the subject's self-management on blood pressure.

It should be noted that since the inclination level data are recorded in measurement result storage areas 129A, 129B, changes in inclination level may be presented in a graph. FIG. 19 shows an exemplary graph displayed in this case.

Referring to FIG. 19, a line graph 81 is displayed on display portion 116. Line graph 81 has a horizontal axis representing the number of times of measurement, and has a vertical axis representing postures (inclination levels). In this way, changes in inclination level can be recognized readily. As shown in FIG. 19, it is preferable to display a broken line or the like indicating whether or not each inclination level constituting line graph 81 is within the recommended inclination range. Further, together with line graph 81 indicating the inclination levels, a graph indicating blood pressure values may be displayed (with the time axes thereof coinciding with each other). In this way, the subject or a medical specialist can know influences of the inclination level (posture for measurement) over blood pressure values.

Alternatively, main unit casing 112 or living body insert portion casing 142 may be provided with, for example, a distance measuring sensor (not shown) for detecting a distance from the trunk of the subject. In this case, when the distance detected by the distance measuring sensor (not shown) falls out of the predetermined distance, CPU 128 may provide notification thereof.

First Variation

Next, a first variation of the first embodiment of the present invention will be described.

The first variation of the present embodiment is different from blood pressure monitor 100 of the foregoing first embodiment only in functions of CPU 128. Only the difference from the first embodiment will be described.

FIG. 20 is a functional block diagram of a blood pressure monitor 100 of the first variation of the first embodiment of the present invention. In the first variation of the present embodiment, a "CPU 128A" is described.

CPU 128A includes a calculating unit 24 instead of search unit 14 included in CPU 128 of the first embodiment. Apart from this, it is the same as the first embodiment.

Calculating unit 24 reads out inclination level data stored in memory 129, and calculates a statistical value of the inclination level data. Specifically, respective frequencies of the inclination levels are calculated. Calculating unit 24 then specifies the most frequent inclination level (mode value), and sends data indicating the inclination level to determining unit 16. In the present embodiment, it is assumed that the frequencies are calculated but another statistical value such as an average value may be employed.

FIG. 21 is a flowchart showing blood pressure measuring/recording processing executed in blood pressure monitor 100 of the first variation of the first embodiment of the present invention. The processing shown in the flowchart of FIG. 21 is also implemented by a program stored in advance in memory 129. CPU 128A reads out and executes the program to implement functions of the blood pressure measuring/recording processing. It should be noted that the same processing as that in the blood pressure measuring/recording processing shown in FIG. 14 and described in the first embodiment is given the same step number. No explanation therefor will be repeated.

Referring to FIG. 21, when the processing of each of steps S2-8 is ended, CPU 128A reads out all the inclination level data recorded in measurement result storage area 129A of memory 129 (step S100). It is also assumed herein that user A was selected in step S2.

Then, calculating unit 24 calculates a measurement frequency for each inclination level based on the inclination level data thus read out (step S110). Based on the result of calculation by calculating unit 24, the most frequent inclination level data (mode value) is output to determining unit 16. When there are a plurality of highly frequent inclination levels, for example, an inclination level specified upon the most recent measurement is employed among the inclination levels.

Determining unit 16 determines whether or not the highly frequent inclination level data falls within the recommended inclination range (step S120). When it is determined that the highly frequent inclination level data is within the recommended inclination range (YES in step S120), the processing goes to step S140. Meanwhile, when it is determined that the highly frequent inclination level data falls out of the recommended inclination range (NO in step S120), the processing goes to step S15.

In step S140, display control unit 18 causes the highly frequent inclination level to be displayed in association with the current inclination level. Namely, display control unit 18 performs processing for displaying, in for example red, a block corresponding to the highly frequent inclination level in block set 30 displayed in step S6 (to indicate the current inclination level).

As such, in the first variation, the most frequent one of the inclination levels specified when the subject has measured blood pressure in past is displayed at the block set in association with the current inclination level. This allows the subject to adjust the posture to come close to the most frequently taken posture for measurement. In this way, the subject can stably take the same posture for measurement (the same inclination level). Accordingly, improved accuracy is achieved in measurement.

It should be noted that also in the first variation, a graph such as one shown in FIG. 19 may be displayed. In this case, the horizontal axis represents the frequency.

Second Variation

Next, a second variation of the first embodiment of the present invention will be described.

The second variation of the present embodiment is different from blood pressure monitor 100 of the foregoing first embodiment only in functions of CPU 128. Only the difference from the first embodiment will be described.

FIG. 22 is a functional block diagram of a blood pressure monitor 100 of the second variation of the first embodiment of the present invention. In the second variation of the present embodiment, a "CPU 128W" is described.

CPU 128B includes a search unit 14A instead of search unit 14 included in CPU 128 of the first embodiment. Further, CPU 128B does not include determining unit 16 included in CPU 128 of the first embodiment. Apart from these, it is the same as the first embodiment.

In the second variation, search unit 14A searches for and reads out data indicating the most recent inclination level falling within the recommended inclination range, among all the inclination level data stored in measurement result storage areas 129A, B of memory 129.

The readout data indicating the inclination level (the most recent one of the inclination levels falling within the recommended inclination range) is output to display control unit 18.

FIG. 23 is a flowchart showing blood pressure measuring/recording processing executed in blood pressure monitor 100 of the second variation of the first embodiment of the present invention. The processing shown in the flowchart of FIG. 23 is also implemented by a program stored in advance in memory 129. CPU 128B reads out and executes the program to implement functions of the blood pressure measuring/recording processing. The same processing as that in the blood pressure measuring/recording processing shown in FIG. 14 and described in the first embodiment is given the same step number. Thus, explanation therefor is not repeated.

Referring to FIG. 23, when the processing in steps S2-8 is ended, search unit 14A searches for and reads out the most recent inclination level data falling within the recommended inclination range, among the inclination level data recorded in measurement result storage area 129A of memory 129 (step S200). It is also assumed herein that user A was selected in step S2.

Next, display control unit 18 causes the inclination level (the most recent one of the inclination levels falling within the recommended inclination range) read out in step S200, to be displayed in association with the current inclination level (step S240). Namely, display control unit 18 performs processing for displaying, in red for example, a block corresponding to the most recent inclination level falling within the recommended range, in the block set displayed in step S6 (to indicate the current inclination level).

As such, according to the second variation of the present embodiment, a past inclination level is surely displayed as long as inclination level data falling within the recommended inclination range is stored in measurement result storage areas 129A, B. As a result, as compared with the first embodiment, a targeted past inclination level is more likely to be displayed.

Third Variation

Next, a third variation of the first embodiment of the present invention will be described.

The third variation of the present embodiment is different from blood pressure monitor 100 of the foregoing first embodiment only in functions of CPU 128. The functions in the third variation are similar to the functions of CPU 128A of the first variation. Only a difference from the first variation of the first embodiment will be described.

FIG. 24 is a functional block diagram of blood pressure monitor 100 of the third variation of the first embodiment of the present invention. In the third variation of the present embodiment, a "CPU 128C" is described.

CPU 128C does not include determining unit 16 included in CPU 128A of the first variation of the first embodiment, but includes an extracting unit 23. Further, instead of calculating unit 24, CPU 128C includes a calculating unit 24A. Apart from these, it is the same as the first variation of the first embodiment.

Extracting unit 23 (searches for and) extracts inclination level data falling within the recommended inclination range, among all the inclination level data recorded in measurement result storage area 129A of memory 129. The inclination level data thus extracted is output to calculating unit 24A.

Calculating unit 24A calculates respective frequencies of the inclination levels extracted by extracting unit 23. Then, calculating unit 24A specifies the most frequent inclination level and outputs the data indicating the most frequent inclination level to display control unit 18.

FIG. 25 is a flowchart showing blood pressure measuring/recording processing executed in blood pressure monitor 100 of the third variation of the first embodiment of the present invention. The processing shown in the flowchart of FIG. 25 is also implemented by a program stored in advance in memory 129. CPU 128C reads out and executes the program to implement the functions of the blood pressure measuring/recording processing. The same processing in the blood pressure measuring/recording processing shown in FIG. 21 and described in the first variation of the first embodiment is given the same step number. No explanation therefor will be repeated.

Referring to FIG. 25, when the processing in steps S2-8 is ended, extracting unit 23 extracts and reads out inclination level data stored in measurement result storage area 129A of memory 129 and falling within the recommended inclination range (step S300). It is also assumed herein that user A was selected in step S2.

Next, calculating unit 24A calculates a measurement frequency for each inclination level based on the inclination level data thus read out (step S310). Based on the result of calculation by calculating unit 24, the most frequent inclination level data falling within the recommended inclination range is output to display control unit 18.

Thereafter, display similar to that in the first variation is provided. When there are a plurality of highly frequent inclination levels, for example, an inclination level specified upon the most recent measurement is employed among these inclination levels.

As such, according to the third variation of the first embodiment, a past inclination level is surely displayed as long as inclination level data falling within the recommended inclination range is recorded in measurement result storage areas 129A, B. As a result, as compared with the first variation of the first embodiment, a targeted past inclination level is highly likely to be displayed.

Second Embodiment

In the above-described first embodiment and the first to third variations thereof, a specified inclination level is surely recorded for each measurement regardless of its value. Hence, upon displaying a past inclination level, it is necessary to determine whether or not inclination level data recorded in memory 129 (measurement result storage areas 129A, B) falls within the recommended inclination range.

However, the present invention is not limited to such an embodiment. For example, an inclination level specified upon measurement may be recorded onto memory 129 only when it falls within the recommended range. Such an embodiment will be described as a second embodiment of the present invention.

The second embodiment of the present invention is different only in functions of CPU 128 of blood pressure monitor 100 of the foregoing first embodiment. Only the difference of blood pressure monitor 100 of the second embodiment from blood pressure monitor 100 of the first embodiment will be described herein, using the reference characters illustrated in FIGS. 1-11 and 13.

FIG. 26 is a functional block diagram of blood pressure monitor 100 of the second embodiment of the present invention. In the second embodiment, a "CPU 128D" is described.

CPU 128D does not include determining unit 16 included in CPU 128 of the first embodiment but includes a determining unit 26 instead. Apart from this, the second embodiment is the same as the first embodiment.

FIG. 27 is a flowchart showing blood pressure measuring/recording processing executed in blood pressure monitor 100 of the second embodiment of the present invention. The processing shown in the flowchart of FIG. 27 is also implemented by a program stored in advance in memory 129. CPU 128D reads out and executes the program to implement functions of the blood pressure measuring/recording processing. The same processing as the blood pressure measuring/recording processing shown in FIG. 14 and described in the first embodiment is given the same step number. No explanation therefor will be repeated.

Referring to FIG. 27, in the second embodiment, the processing of determination in step S12 is omitted. Hence, in step S14, the most recent inclination level searched in step S10 is surely displayed.

Meanwhile, processing of determination of step S19 is inserted after step S18. In step S19, determining unit 26 determines whether or not the current inclination level, i.e., the inclination level specified in step S4 falls within the recommended inclination range. The inclination level used for the determination herein is also preferably the inclination level specified upon the processing in step S18.

When it is determined that the current inclination level is within the recommended inclination range (YES in step S19), the current blood pressure data (and the pulse rate data) and the inclination level data are recorded onto measurement result storage area 129A (step S20A). More specifically, measurement date/time data DTn, systolic blood pressure data SBPn, diastolic blood pressure data DBPn, pulse rate data PLSn, and inclination level data AGn are stored in measurement result storage area 129A corresponding to the user (user A) selected in step S2.

On the other hand, when it is determined that the current inclination level is out of the recommended inclination range (NO in step S19), only the current blood pressure data (and the pulse rate data) are recorded onto measurement result storage area 129A (step S20B). More specifically, measurement date/time data DTn, systolic blood pressure data SBPn, diastolic blood pressure data DBPn, and pulse rate data PLSn are stored in measurement result storage area 129A corresponding to the user (user A) selected in step S2, but inclination level data AGn is not stored therein.

After the processing in step S20A or S20B is ended, processing in step S22 is executed.

As such, in the second embodiment of the present invention, only inclination level data falling within the recommended inclination range are stored in measurement result storage areas 129A, B. Accordingly, processing for displaying a past inclination level before starting measurement can be faster. Thus, the subject can immediately take an optimal posture for measurement.

In the processing in the second embodiment, it is assumed that the control for displaying as described in the first embodiment (displaying the most recent inclination level) is performed, but the control for displaying as described in the first variation of the first embodiment (displaying the highly frequent inclination level) may be performed.

The above description assumes that in the first embodiment and the first to third variations thereof as well as the second embodiment of the present invention, the processing (steps S16, S18) for measuring blood pressure is started when a subject's instruction to start measurement is detected using control portion 114. However, in each embodiment and variation, the processing for measuring it may be started when a displayed past inclination level (for example, the most recent inclination level falling within the recommended range) and a current inclination level specified based on a signal from angular sensor 160 coincide with each other. In this way, the same posture can be taken more securely for measurement. This eliminates influences of a difference (deviation) in posture over measurement values completely, thus facilitating a subject's self-management on blood pressure.

The embodiments has been described with reference to blood pressure monitor 100 provided with the automatic cuff winding mechanism for automatically winding (applying) cuff 145 around a subject's upper arm, but the present invention is not limited to such a blood pressure monitor. For example, there may be provided a portable blood pressure monitor capable of measuring blood pressure from a subject's wrist around which its cuff is wound. Also in such a blood pressure monitor, the same function as described above can be attained by providing an angular sensor or the like for measuring an inclination angle of the cuff relative to the horizontal plane so as to detect a difference from the height of the subject's heart.

It should be considered that the embodiments disclosed herein are illustrative and non-restrictive in any respect. The scope of the present invention is defined by the scope of claims, and is intended to include any modifications within the scope and meaning equivalent to the terms of the claims.

The invention claimed is:

1. A blood pressure monitor comprising:
   a cuff to be wound around a living body of a subject;
   a measuring unit that measures blood pressure with said cuff wound around the living body of said subject;
   a detecting unit that detects an inclination angle of said cuff;
   a first enclosure to be placed on a placement table;
   a second enclosure having an approximately cylindrical shape, located on said first enclosure in a non-use state, and having an inner peripheral surface on which said cuff is disposed; and
   a connecting portion that connects said second enclosure to said first enclosure in a freely movable manner such that upon applying said cuff to said subject with said first enclosure being placed on said placement table, said second enclosure is movable toward said subject from a location where said second enclosure is in the non-use state,
   wherein said detecting unit detects an inclination angle of said second enclosure relative to one of said first enclosure and a horizontal plane;
   a memory that stores a plurality of predetermined inclination levels;
   a specifying unit that specifies a current inclination level of the subject among the plurality of predetermined inclination levels upon measurement by said measuring unit, based on a result of detection by said detecting unit,
   wherein the memory stores therein the current inclination level of the subject specified by said specifying unit, in association with blood pressure data of the subject measured by said measuring unit;
   a notifying unit that, during the blood pressure measurement, provides notification of at least one past inclination level of the plurality of predetermined inclination levels stored for the subject in said memory and said current inclination level of the subject, in association with each other;
   a statistics calculating unit that calculates a statistical value of said plurality of predetermined inclination levels stored for the subject in said memory, wherein said notifying unit provides notification of said past inclination level based on a result of calculation by said statistics calculating unit; and
   a display portion that displays a block set comprising a plurality of predetermined blocks, the plurality of predetermined blocks corresponding to the plurality of predetermined inclination levels.

2. The blood pressure monitor according to claim 1,
   wherein said statistics calculating unit includes a frequency calculating unit that calculates respective frequencies of said plurality of inclination levels, and
   wherein as a result of calculation by said frequency calculating unit, said notifying unit provides notification of a most frequent inclination level as said past inclination level.

3. The blood pressure monitor according to claim 1, further comprising:
   an extracting unit that extracts inclination levels falling within a predetermined range, among said plurality of predetermined inclination levels stored for the subject in said memory,
   wherein the statistics calculating unit calculates a statistical value of the inclination levels extracted by said extracting unit,
   wherein said notifying unit provides notification of said past inclination level based on a result of calculation by said statistics calculating unit.

4. The blood pressure monitor according to claim 3,
   wherein said statistics calculating unit includes a frequency calculating unit that calculates respective frequencies of said inclination levels extracted, and
   wherein as a result of calculation by said frequency calculating unit, said notifying unit provides notification of a most frequent inclination level as said past inclination level.

5. The blood pressure monitor according to claim 1, further comprising a determining unit that determines whether or not said specified current inclination level of the subject falls within a predetermined range,
   wherein when said determining unit determines that said current inclination level of the subject falls within said predetermined range, said memory stores said current inclination level of the subject therein.

6. The blood pressure monitor according to claim 1, wherein said notifying unit comprises:
   a display control unit that performs control that displays said past inclination level and said current inclination level of the subject in association with each other; and
   a display that displays based on an output from said display control unit.

7. The blood pressure monitor according to claim 6, wherein said display control unit performs control that displays in a graph said plurality of inclination levels stored for the subject in said memory.

* * * * *